United States Patent [19]

Klausener et al.

[11] Patent Number: 5,292,889
[45] Date of Patent: Mar. 8, 1994

[54] FUNGICIDAL AND INSECTICIDAL SUBSTITUTED-HETEROCYCLYL-ACRYLIC ESTERS

[75] Inventors: Alexander Klausener, Krefeld; Dieter Berg, Wuppertal; Thomas Seitz, Monheim; Wilhelm Brandes, Leichlingen; Stefan Dutzmann, Duesseldorf; Gerd Hänssler, Leverkusen; Ulrike Wachendorff-Neumann, Monheim, all of Fed. Rep. of Germany

[73] Assignee: Bayer Aktiengesellschaft, Leverkusen, Fed. Rep. of Germany

[21] Appl. No.: 895,961

[22] Filed: Jun. 9, 1992

Related U.S. Application Data

[62] Division of Ser. No. 604,739, Oct. 26, 1990, Pat. No. 5,137,898.

[30] Foreign Application Priority Data

Nov. 28, 1989 [DE] Fed. Rep. of Germany ....... 3939238

[51] Int. Cl.$^5$ ........................................... C07D 417/02
[52] U.S. Cl. .................................................... 548/181
[58] Field of Search ......................................... 548/181

[56] References Cited

U.S. PATENT DOCUMENTS 5,182,295  1/1993  Benoit ................................. 514/365

Primary Examiner—Robert Gerstl
Attorney, Agent, or Firm—Sprung Horn Kramer & Woods

[57] ABSTRACT

Fungicidal and insecticidal substituted-heteroycylacrylic esters of the formula

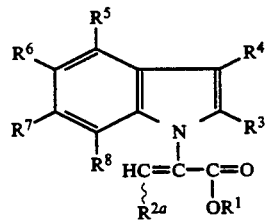

in which
  $R^1$ represents alkyl, or represents unsubstituted- or substituted aralkyl,
  $R^{2a}$ represents hydrogen, dialkylamino, alkoxy or alkylthio, or represents in each case unsubstituted or substituted aralkyloxy or arylalkylthio, and
  $R^7$ represents one of 3 Claims, No Drawings

FUNGICIDAL AND INSECTICIDAL SUBSTITUTED-HETEROCYCLYL-ACRYLIC ESTERS

This is a division of application Ser. No. 07/604,739, filed Oct. 26, 1990, now U.S. Pat. No. 5,137,898.

The invention relates to new acrylic esters which are substituted by a heterocycle, to several processes for their preparation, to their use for combating pests, and to new intermediates.

It is known that certain substituted acrylic esters, such as, for example, the compound methyl 3-methoxy-2-(2-methylphenyl)acrylate have fungicidal properties (cf., for example, European Patent 178,826).

It is furthermore known that certain alkoxy acrylic esters which are substituted in the 2-position by a 1-indolyl radical are fungicidally active (cf. European Patent 274,825).

However, the effectiveness of these previously known compounds is not entirely satisfactorily in all fields of application, in particular when low application rates and concentrations are used.

New acrylic esters which are substituted by a heterocycle of the general formula (I) have been found,

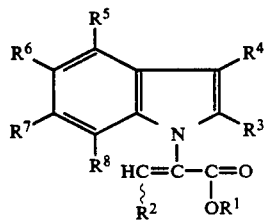

(I)

in which
R¹ represents alkyl, or represents unsubstituted or substituted aralkyl,
R² represents dialkylamino, alkoxy or alkylthio., or represents in each case unsubstituted or substituted aralkyloxy or arylalkylthio,
R³ and R⁴ in each case independently of one another represent hydrogen, cyano, halogen or alkyl,
R⁵, R⁶ and R⁸ independently of one another in each case represent hydrogen, halogen, cyano, nitro, in each case straight-chain or branched alkyl, alkoxy or alkylthio, each of which has 1 to 4 carbon atoms- or represent alkylidenedioxy having 1 to 6 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, cycloalkyl having 3 to 7 carbon atoms, divalent alkanediyl having 3 to 5 carbon atoms, or aryl, aralkyl, aryloxy, arylthio, aralkyloxy or aralkylthio, each of which has 6 to 10 carbon atoms in the aryl moiety and where appropriate 1 to 4 carbon atoms in the straight-chain or branched alkyl moiety and each of which is unsubstituted or monosubstituted or polysubstituted in the aryl moiety by identical or different substitutents from the series comprising halogen, alkyl, alkoxy, alkylthio, halogenoalkyl, halogenoalkoxy or halogenoalkylthio, each of which has 1 to 4 carbon atoms and where appropriate 1 to 9 identical or different halogen atoms, or represent heteroarylalkyl, heteroaryloxy, heteroarylthio or heteroaryl, each of which has 2 to 9 carbon atoms and 1 to 4 identical or different hetero atoms—in particular nitrogen, oxygen and/or sulphur—in the heteroaryl moiety and where appropriate 1 to 4 carbon atoms in the straight-chain or branched alkyl moiety and each of which is optionally monosubstituted or polysubstituted in the heteroaryl moiety by identical or different substituents from the series comprising halogen, alkyl, alkoxy, alkylthio, halogenoalkyl, halogenoalkoxy or halogenoalkylthio, each of which has 1 to 4 carbon atoms and where appropriate 1 to 9 identical or different halogen atoms, and R⁷ represents one of the following groups

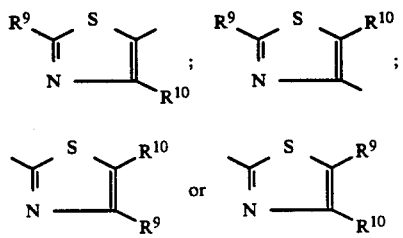

where
R⁹ and R¹⁰ in each case independently of one another represent hydrogen, halogen, cyano, nitro, alkyl, alkoxy, alkylthio, halogenoalkyl, alkoxycarbonyl or dialkylaminocarbonyl, or represent in each case unsubstituted or substituted aryl, aralkyl, aryloxy, arylthio, aralkyloxy, aralkylthio, hetaryl, hetaryloxy or hetarylthio.

The compounds of the formula (I) can be present as geometric isomers or mixtures of isomers of various compositions. The invention covers the pure isomers as well as the mixtures of isomers.

It has furthermore been found that the..new acrylic esters which are substituted by a heterocycle, of the general formula (I)

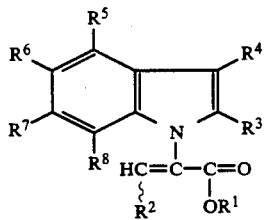

(I)

in which R¹ to R⁸ has the abovementioned meanings are obtained by one of the processes described below:

a) substituted acrylic esters of the general formula (Ia)

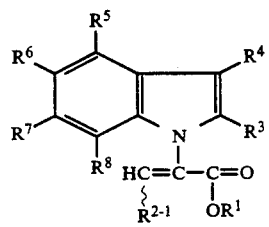

(Ia)

in which $R^1$, $R^3$, $R^4$, $R^5$, $R^6$, $R^7$ and $R^8$ have the abovementioned meanings and $R^{2-1}$ represents alkoxy or unsubstituted or substituted aralkyloxy, are obtained when hydroxyacrylic esters or alkali metal salts thereof of the formula (II)

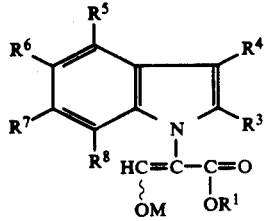
(II)

in which

M represents hydrogen or an alkali metal cation and $R^1$, $R^3$, $R^4$, $R^5$, $R^6$, $R^7$ and $R^8$ have the abovementioned meanings, are reacted with alkylating agents of the formula (III)

$$R^{11}-E^1 \quad (III)$$

in which $R^{11}$ represents alkyl or unsubstituted or substituted aralkyl and $E^1$ represents an electron-attracting leaving group, if appropriate in the presence of a diluent and if appropriate in the presence of a reaction auxiliary;

b) substituted acrylic esters of the general formula (Ib)

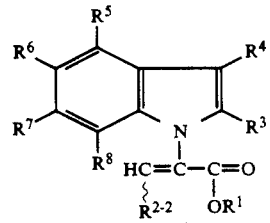
(Ib)

in which $R^1$, $R^3$, $R^4$, $R^5$, $R^6$, $R^7$ and $R^8$ have the abovementioned meanings and $R^{2-2}$ represents dialkylamino, are obtained when substituted acetic esters of the formula (IV)

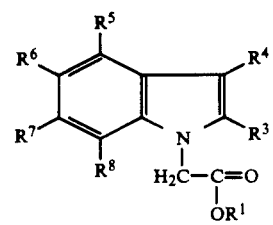
(IV)

in which in which $R^1$, $R^3$, $R^4$, $R^5$, $R^6$, $R^7$ and $R^8$ have the abovementioned meanings, are reacted with formamides of the formula (Va)

(Va)

in which $R^{2-2}$ has the abovementioned meaning, or with formamide derivatives of the formula (Vb)

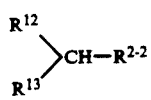
(Vb)

in which $R^{12}$ and $R^{13}$ independently of one another represent alkoxy or dialkylamino and $R^{2-2}$ has the abovementioned meaning, if appropriate in the presence of a diluent;

c) substituted acrylic esters of the formula (Ic)

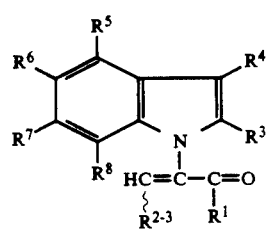
(Ic)

in which $R^1$, $R^3$, $R^4$, $R^5$, $R^6$, $R^7$ and $R^8$ have the abovementioned meanings and $R^{2-3}$ represents alkylthio or unsubstituted or substituted aralkylthio, are obtained when ketocarboxylic acid derivatives of the formula (VI)

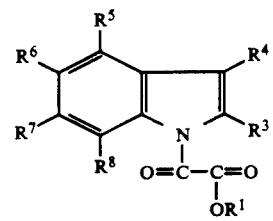
(VI)

in which $R^1$, $R^3$, $R^4$, $R^5$, $R^6$, $R^7$ and $R^8$ have the abovementioned meanings, are reacted with organometal compounds of the formula (VII)

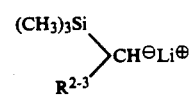
(VII)

in which $R^{2-3}$ has the abovementioned meaning, if appropriate in the presence of a diluent;

d) substituted acrylic esters of the formula (Ic) are furthermore obtained when substituted acrylic esters of the formula (VIII)

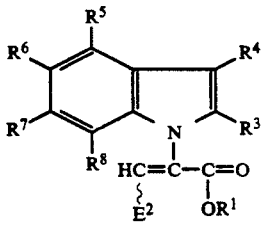

(VIII)

in which
R$^1$, R$^3$, R$^4$, R$^5$, R$^6$, R$^7$ and R$^8$ have the abovementioned meanings and
D$^2$ represents an electron-attracting leaving group, are reacted with thiols of the formula (IX)

R$^{2-3}$—H (IX)

in which R$^{2-3}$ has the abovementioned meaning, if appropriate in the presence of a diluent and if appropriate in the presence of a reaction auxiliary.

Finally, it has been found that the new acrylic esters and also the acetic esters which are substituted on the heterocycle of the general formula (I) or formula (IV) respectively have a good action against pests.

Surprisingly, the substituted acrylic esters of the general formula (I) according to the invention have an insecticidal action and a considerably better fungicidal effectiveness than the acrylic esters known from the prior art, such as, for example, the compound methyl 3-methoxy-2-(2-methylphenyl)-acrylate, which are compounds of a similar structure and similar type of action.

Formula (I) provides a general definition of the new acrylic esters which are substituted on the heterocycle according to the invention. Unless otherwise defined, preferred substituents or ranges of the radicals listed in this formula and the formulae mentioned below are illustrated in the following text:

Alkyl in the definitions of R$^1$, R$^3$, R$^4$, R$^5$, R$^6$, R$^8$, R$^9$ and R$^{10}$ in the general formulae represents straight-chain or branched alkyl having preferably 1 to 8, particularly preferably 1 to 6 and in particular 1 to 4, carbon atoms. The following may be mentioned by way of example and as being preferred: methyl, ethyl, n-propyl, i-propyl, n-butyl, sec-butyl, i-butyl, t-butyl, n-pentyl, i-pentyl, t-pentyl and n-hexyl.

Dialkyl in the definition of R$^2$ or in combinations such as dialkylaminocarbonyl in the definition of R$^9$ and R$^{10}$ represents an amino group having 2 alkyl groups which can in each case be straight-chain or branched and identical or different and which contain preferably in each case 1 to 6, in particular 1 to 4, carbon atoms, methyl, ethyl, n- and i-propyl being mentioned.

Dimethylamino, diethylamino, di-n-propylamino and di-i-propylamino may be mentioned by way of example as being preferred.

The term unsubstituted or substituted aryl in the definition of R$^5$, R$^6$, R$^8$, R$^9$ and R$^{10}$ in the general formulae is to be understood as meaning aryl having preferably 6 to 10 carbon atoms in the aryl moiety. Unsubstituted or substituted phenyl or naphthyl, in particular phenyl, may be mentioned by way of example and as being preferred.

Unsubstituted or substituted aralkyl in the definitions of R$^1$, R$^5$, R$^6$, R$^8$, R$^9$ and R$^{10}$ preferably contains 1 to 6, in particular 1 to 4, carbon atoms in the straight-chain or branched alkyl moiety and preferably phenyl as the aryl moiety. Aralkyl groups which may be mentioned by way of example and as being preferred are benzyl and phenethyl.

In general, heteroaryl in the definition of R$^5$, R$^6$, R$^8$, R$^9$ and R$^{10}$ represents a 5- to 6-membered ring which contains 1 to 4, preferably 1 to 3, identical or different hetero atoms. Hetero atoms which may preferably be mentioned are oxygen, sulphur and nitrogen;- the following may be mentioned by way of example and as being preferred: pyrimidinyl, pyrrolyl, isothiazolyl, oxazolyl, pyridyl, thienyl, furyl, pyridazinyl, pyrazinyl, isoxazolyl, thiazolyl and pyrazolyl.

The term alkoxy in the definition of R$^2$, R$^5$, R$^6$, R$^8$, R$^9$ and R$^{10}$ in the general formulae is understood as meaning straight-chain or branched alkoxy having preferably 1 to 6, in particular 1 to 4, carbon atoms. The following may be mentioned by way of example and as being preferred: methoxy, ethoxy, propoxy, butoxy as well as their isomers, i-propoxy, i-, s- and t-butoxy.

Halogen in the definitions R$^3$, R$^4$, R$^5$, R$^6$, R$^8$, R$^9$ and R$^{10}$ represents fluorine, chlorine, bromine and iodine, preferably fluorine, chlorine and bromine, particularly preferably fluorine and chlorine.

In combinations such as alkoximinoalkyl, alkyl in the definitions R$^5$, R$^6$ and R$^8$ represents straight-chain or branched alkyl, preferably having 1 to 4 carbon atoms, with methyl, ethyl and t-butyl being very particularly preferred. The enumeration given by way of example corresponds to the one further above.

Alkylthio in the definitions R$^2$, R$^5$, R$^6$, R$^8$, R$^9$ and R$^{10}$ represents straight-chain or branched alkylthio having preferably 1 to 6 carbon atoms, for example it is understood as meaning the following groups: methylthio ethylthio, propylthio, butylthio and pentylthio as thio, i-, s- and t-butylthio, 1-methyl-butylthio, 2-methyl-butylthio and 3-methyl-butylthio. Preferred alkylthio radicals contain 1 to 4 carbon atoms. Methylthio, ethylthio, n-, i-, s-propylthio and n-, i-, s- and t-butylthio are particularly preferred.

Halogenoalkyl and halogenoalkoxy in the definitions of R$^5$, R$^6$, R$^8$, R$^9$ and R$^{10}$ represent straight-chain or branched halogenoalkyl or halogenoalkoxy having in each case 1 to 6, in particular 1 to 4, carbon atoms, particularly preferably having 1 or 2 carbon atoms and in each case 1 to 13, in particular 1 to 9, preferably 1 to 5, identical or different halogen atoms as defined under halogen; the following may be mentioned by way of example and as being preferred: fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chlorodifluoromethyl, trifluorochloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy and trifluorochloroethoxy.

Halogenoalkylthio in the definitions of R$^5$, R$^6$ and R$^8$ represents straight-chain or branched halogenoalkylthio having in each case 1 to 4 carbon atoms, particularly preferably having 1 or 2 carbon atoms and in each case 1 to 9, preferably 1 to 5, identical or different halogen atoms as defined under halogen; the following may be mentioned by way of example and as being preferred: fluoromethylthio, chloromethylthio, bromomethylthio, fluoroethylthio, chloroethylthio, bromoethylthio, fluoropropylthio, chloropropylthio, bromopropylthio, fluorobutylthio, chlorobutylthio, bromobutylthio, fluoro-i-propylthio, chloro-i-propylthio, difluoromethylthio, thio, difluoroethylthio, trifluoroethylthio, tetrafluoroethylrhio, trichloroethylthio, chlorodifluoromethylthio and trifluorochloroethylthio.

Alkoxycarbonyl in the definitions $R^5$, $R^6$, $R^8$, $R^9$ and $R^{10}$ represents straight-chain or branched alkoxycarbonyl having 1 to 6, in particular 1 to 4, preferably 1 or 2, carbon atoms in the alkoxy radical; the following may be mentioned by way of example and as being preferred: methoxycarbonyl, ethoxycarbonyl, n-propoxycarbonyl, i-propoxycarbonyl, n-, i-, s- and t-butoxycarbonyl.

Cycloalkyl in the definitions $R^5$, $R^6$ and $R^8$ represents cycloalkyl having preferably 3 to 7, in particular 3, 5 or 6, carbon atoms. Unsubstituted or substituted cyclopropyl, cyclopentyl and cyclohexyl may be mentioned by way of example and as being preferred.

Unsubstituted or substituted aryloxy and arylthio in the definitions of $R^5$, $R^6$, $R^8$, $R^9$ and $R^{10}$ in the general formulae represent aryl having preferably 6 to 10 carbon atoms in the aryl moiety. Unsubstituted or substituted phenoxy or phenylthio, in particular phenoxy, may be mentioned as being preferred.

In the definitions $R^2$, $R^5$, $R^6$, $R^8$, $R^9$ and $R^{10}$, unsubstituted or substituted aralkyloxy or aralkylthio contain preferably 1 to 6 carbon atoms in the straight-chain or branched alkyl moiety and preferably phenyl as the aryl moiety. Preferred aralkyl groups which may be mentioned are benzyl and phenethyl.

In the definition of $R^5$, $R^6$, $R^8$, $R^9$ and $R^{10}$, heteroarylalkyl, heteroaryloxy and heteroarylthio generally represent a 5- to 6-membered ring which contains one or more hetero atoms, preferably 1 to 3, in particular 1 or 2 identical or different hetero atoms. Hetero atoms which may be mentioned as preferred are oxygen, sulphur and nitrogen; the following may be mentioned by way of example and as being preferred: pyridyl, thienyl, furyl, pyridazinyl, pyrazinyl, isoxazolyl, thiazolyl, pyridylmethyl, thienylmethyl, furylmethyl, furylmethyl, pyridyloxy, thienyloxy, furyloxy, pyridazinyloxy, pyrazinyloxy, isoxazolyloxy, thiazolyloxy, pyridylmethyloxy, thienylmethyloxy, furylmethyloxy, pyridylthio, thienylthio, furylthio, pyridazinylthio, pyrazinylthio, isoxazolylthio, thiazolylthio, pyridylmethylthio, thienylmethylthio and furylmethylthio.

The substituents for the aryl radicals as such or in combinations such as arylalkyl, aryloxy, arylthio, aralkyloxy, aralkylthio, and for the heterocyclic rings, such as heteroarylalkyl and heteroaryl, have the meanings given hereinbelow.

Halogen as a substituent generally represents fluorine, chlorine, bromine and iodine, preferably fluorine, chlorine and bromine, particularly preferably fluorine and chlorine.

Alkyl as a substituent or in combinations such- as alkoximinoalkyl generally represents straight-chain or branched alkyl, preferably having 1 to 6, particularly preferably having 1 to 4, carbon atoms with methyl, ethyl, i-propyl and t-butyl being very particularly preferred. The enumeration given by way of example corresponds to that further above.

Alkoxy as a substituent or in combinations such as alkoximinoalkyl generally represents straight-chain or branched alkoxy having 1 to 6, particularly preferably 1 to 3, carbon atoms per alkyl radical; the following may be mentioned by way of example and as being preferred: methoxy, ethoxy and n- and i-propoxy.

Alkylthio as a substituent in the radicals generally represents straight-chain or branched alkylthio having preferably 1 to 6 carbon atoms, for example it is understood as meaning the following groups: methylthio, ethylthio, propylthio, butylthio and pentylthio as well as their isomers, such as, for example, i-propylthio, i-, s- and t-butylthio, 1-methyl-butylthio, 2-methyl-butylthio and 3-methyl-butylthio. Preferred alkylthio radicals contain 1 to 4 carbon atoms. Methylthio, ethylthio, n-, i-, s-propylthio and n-, i-, s- and t-butylthio are particularly preferred.

Halogenoalkyl and halogenoalkoxy as substituents in the radicals generally represent straight-chain or branched halogenoalkyl or halogenoalkoxy, each of which has 1 to 4 carbon atoms, particularly preferably 1 or 2 carbon atoms, and in each case 1 to 9, preferably 1 to 5, identical or different halogen atoms as defined under halogen; the following may be mentioned by way of example: fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chlorodifluoromethyl, trifluorochloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy and trifluorochloroethoxy.

Halogenoalkylthio as a substituent in the radicals generally represents straight-chain or branched halogenoalkylthio, each of which has 1 to 4 carbon atoms, particularly preferably 1 or 2 carbon atoms, and in each case 1 to 9, preferably 1 to 5, identical or different halogen atoms as defined under halogen; the following may be mentioned by way of example: fluoromethylthio, chloromethylthio, bromomethylthio, fluoroethylthio, chloroethylthio, bromoethylthio, fluoropropylthio, chloropropylthio, bromopropylthio, fluorobutylthio, chlorobutylthio, bromobutylthio, fluoro-i-propylthio, chloro-i-propylthio, difluoromethylthio, trifluromethylthio, dichloromethylthio, trichloromethylthio, difluoroethylthio, trifluoroethylthio, tetrafluoroethylthio, trichloroethylthio, chlorodifluromethylthio and trifluorochloroethylthio.

The definitions given here also apply -in a corresponding manner to the preferred combinations of radicals given hereinbelow.

Preferred compounds of the formula (I) are those in which $R^1$ represents straight-chain or branched alkyl having 1 to 6 carbon atoms, or represents benzyl, $R^2$ represents dialkylamino having in each case 1 to 6 carbon atoms in the individual straight-chain or branched alkyl moieties, in each case straight-chain or branched alkoxy or alkylthio having 1 to 6 carbon atoms, or represents benzyloxy or benzylthio, each of which is unsubstituted or monosubstituted or polysubstituted by identical or different substitutents, suitable phenyl substituents being: halogen, in each case straight-chain or branched alkyl, alkoxy or alkylthio each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, or cycloalkyl having 3 to 7 carbon atoms, $R^3$ and $R^4$ in each case independently of one another represent hydrogen, cyano, fluorine, chlorine, bromine or straight-chain or branched alkyl having 1 to 6 carbon atoms, $R^5$, $R^6$ and $R^8$ independently of one another represent hydrogen, fluorine, chlorine, bromine, methyl, ethyl, n- or i-propyl, n-, i-, s- or t-butyl, methoxy, ethoxy, n- or i-propoxy, methylenedioxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoxyiminoethyl, cyclopentyl, cyclohexyl, divalent 1,3-propanediyl or 1,4-butanediyl, or represents phenyl, benzyl, phenoxy, benzyloxy, phenylthio or benzylthio, each of which is optionally monosubstituted to trisubstituted in the phenyl moiety by identical or different substituents from the series comprising fluorine, chlorine, bromine, methyl, ethyl, methoxy, ethoxy, methylthio, trifluoromethyl, difluoromethoxy, trifluoromethoxy and/or trifluoromethylthio, and $R^7$ represents one of the following groups

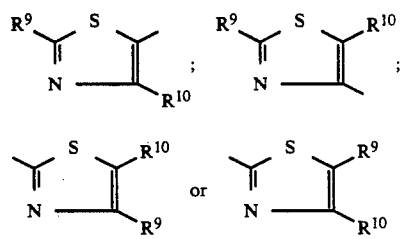

where
$R^9$ and $R^{10}$ in each case independently of one another represent hydrogen, fluorine, chlorine, bromine, cyano, in each case straight-chain or branched alkyl, alkoxy, alkylthio or halogenoalkyl having 1 to 6 carbon atoms and where appropriate 1 to 13 identical or different halogen atoms, or represent straight-chain or branched alkoxycarbonyl having 1 to 6 carbon atoms in the alkoxy moiety, or dialkylaminocarbonyl which has 1 to 4 carbon atoms in each alkyl moiety, each of the individual alkyl moieties being straight-chain or branched and substituted by identical or different substituents, or represents phenyl, benzyl, phenyloxy, phenylthio, benzyloxy or benzylthio, each of which is unsubstituted or monosubstituted to trisubstituted by identical or different substituents, or represent 5- or 6-membered heteroaryl which contains 1 to 3 hetero atoms from the series comprising nitrogen, oxygen or sulphur and which is unsubstituted or monosubstituted or disubstituted by identical or different substituents, suitable substituents in each case being halogen, alkyl, alkoxy, alkylthio, halogenoalkyl, halogenoalkyloxy, halogenoalkylthio, each of which has 1 to 4 carbon atoms and where appropriate 1 to 9 identical or different halogen atoms, dialkylamino or dialkylaminocarbonyl, each of which has 1 to 4 carbon atoms in each of the straight-chain or branched alkyl moieties, 1,3-propanediyl, 1,4-butanediyl, or phenyl or benzyl which are unsubstituted or monosubstituted to disubstituted by identical or different substituents, suitable substituents in each case being halogen or phenyloxy.

Particularly preferred compounds of the formula (I), are those in which $R^1$ represents straight-chain or branched alkyl having 1 to 4 carbon atoms, $R^2$ represents dialkylamino having 1 to 4 carbon atoms in each of the individual straight-chain or branched alkyl moieties, in each case straight-chain or branched alkoxy or alkylthio having 1 to 4 carbon atoms, or represents benzyloxy or benzylthio, $R^3$ and $R^4$ are identical or different and represent hydrogen, cyano, fluorine, chlorine, bromine, methyl, ethyl, n- or i-propyl or n-, i-, s- or t-butyl, $R^5$ and $R^6$ are identical or different and represent hydrogen, fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl or cyclohexyl, or together represent a methylenedioxy, 1,3-propanediyl or 1,4-butanediyl group, $R^7$ represents one of the following groups

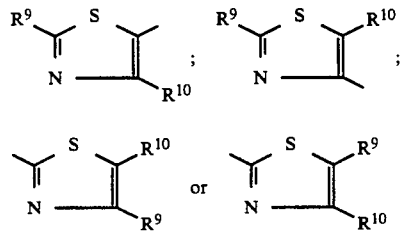

where
$R^9$ represents hydrogen, straight-chain or branched alkyl having 1 to 6 carbon atoms, or phenyl or benzyl, each of which is unsubstituted or monosubstituted to trisubstituted by identical or different substituents, or represents 5- or 6-membered heteroaryl which contains 1 to 3 hetero atoms from the series comprising nitrogen, oxygen or sulphur, and which is monosubstituted or disubstituted by identical or different substituents, suitable substituents in each case being halogen, methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, halogenoalkyl, halogenoalkoxy or halogenoalkylthio, each of which has 1 or 2 carbon atoms and 1 to 5 identical or different fluorine or chlorine atoms, or dialkylamino or dialkylaminocarbonyl having 1 or 2 carbon atoms in the individual alkyl moieties, or phenyl, phenoxy or benzyl which is unsubstituted or monosubstituted to disubstituted by identical or different substituents, suitable substituents in each case being fluorine, chlorine or phenoxy, and $R^{10}$ represents hydrogen, straight-chain or branched alkyl having 1 to 4 carbon atoms, chlorine, bromine, cyano, methoxycarbonyl, ethoxycarbonyl, , dimethylaminocarbonyl, diethylaminocarbonyl, methoxy, ethoxy, methylthio or ethylthio, and $R^8$ represents hydrogen, fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl or ethoxycarbonyl.

Very particularly preferred compounds of the formula (I) are those in which $R^1$ represents methyl or ethyl, $R^2$ represents dimethylamino, diethylamino, methoxy, ethoxy, methylthio, ethylthio, benzyloxy or benzylthio, $R^3$ represents hydrogen, chlorine or methyl, $R^4$ represents hydrogen, chlorine or methyl, $R^5$ represents hydrogen, fluorine, chlorine, bromine, methyl, ethyl, trifluoromethyl, methoxycarbonyl or ethoxycarbonyl, $R^6$ represents hydrogen, fluorine, chlorine, bromine, methyl, ethyl, methoxy, ethoxy, methylthio, trifluoromethyl, methoxycarbonyl or ethoxycarbonyl, or $R^5$ and $R^6$ together represent a methylenedioxy, 1,3-propanediyl or 1,4-butanediyl group, $R^7$ represents one of the following groups

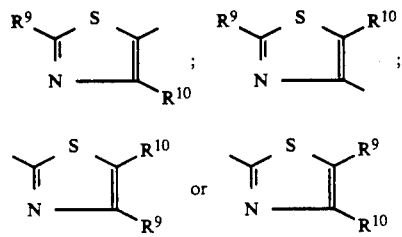

where $R^9$ represents hydrogen, methyl, ethyl, n- or i-propyl, n-, s-, i-butyl, n- or i-pentyl, n-hexyl, benzyl, o-, m- or p-chlorobenzyl, o-, m- or p-methylbenzyl, phenyl or phenyl which is in each case monosubstituted to trisubstituted by identical or different substituents, or represents 5- or 6-membered heteroaryl which contains 1 or 2 hetero atoms from the series comprising nitrogen, oxygen or-sulphur and which is monosubstituted or disubstituted by identical or different substituents, suitable substituents in each case being fluorine, chlorine, methyl, ethyl, t-butyl, methoxy, ethoxy, methylthio, trifluoromethyl, trifluoromethoxy, trifluoromethylthio, phenyl, p-chlorophenyl, m- or p-phenoxyphenyl or benzyl, and $R^{10}$ represents hydrogen, methyl, ethyl, chlorine, bromine, methoxycarbonyl or ethoxycarbonyl, and $R^8$ represents hydrogen, methyl or ethyl.

In addition to the compounds mentioned in the Preparation Examples, the following acrylic esters which are substituted on the heterocycle of the general formula (I) may be mentioned individually:

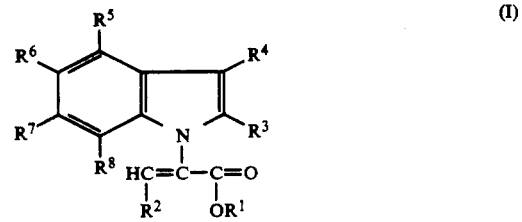

TABLE 1

| $R^1$ | $R^2$ | $R^3$ | $R^4$ | $R^5$ | $R^6$ | $R^7$ | $R^8$ |
|---|---|---|---|---|---|---|---|
| $C_2H_5$ | $OCH_3$ | H | H | H | H | (thiazolyl-phenyl) | H |
| $C_2H_5$ | $OCH_3$ | H | H | H | H | (thiazolyl-pyridyl) | H |
| $C_2H_5$ | $OCH_3$ | H | H | H | H | $H_3C$-(bis-thiazolyl) | H |
| $CH_3$ | $SCH_3$ | H | H | H | H | (thiazolyl-phenyl) | H |

TABLE 1-continued

| R¹ | R² | R³ | R⁴ | R⁵ | R⁶ | R⁷ | R⁸ |
|---|---|---|---|---|---|---|---|
| CH₃ | SCH₃ | H | H | H | H | Br-C(=N-)(-S-C(=N-C(CH₃)=)-pyridyl) | H |
| CH₃ | SCH₃ | H | H | H | H | -C(=N-)(-S-CH=C(-N=C(CH₃)-S-)-) | H |
| CH₃ | N(CH₃)₂ | H | H | H | H | Cl-C(=N-)(-S-C(3,4,5-trichlorophenyl)) | H |
| CH₃ | OCH₃ | H | H | CH₃ | H | -C(=N-)(-S-C(4-fluorophenyl)) | H |
| CH₃ | OCH₃ | H | H | CH₃ | H | -C(=N-)(-S-C(4-fluorophenyl)) | H |
| CH₃ | OCH₃ | H | H | Cl | H | -C(=N-)(-S-C(6-chloropyridyl)) | H |
| CH₃ | OC₂H₅ | H | H | Cl | H | -C(=N-)(-S-CH=C(-N=C(CH₃)-S-)-) | H |
| CH₃ | OCH₃ | CH₃ | H | H | H | -C(=N-)(-S-C(4-chlorophenyl)) | H |
| CH₃ | OCH₃ | CH₃ | H | H | H | -C(=N-)(-S-C(3,4-dimethylphenyl)) | H |
| CH₃ | OCH₃ | Cl | H | H | H | -C(=N-)(-S-CH=C(3,4-dichlorophenyl)) | H |
| CH₃ | OCH₃ | H | CH₃ | H | H | -C(=N-)(-S-CH=C(2,4-difluorophenyl)) | H |

TABLE 1-continued
| R¹ | R² | R³ | R⁴ | R⁵ | R⁶ | R⁷ | R⁸ |
|---|---|---|---|---|---|---|---|
| CH₃ | OCH₃ | H | CH₃ | H | H | 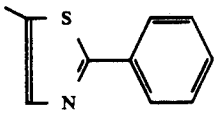 | H |
| CH₃ | OCH₃ | H | H | H | H | 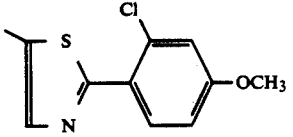 | H |
| CH₃ | OCH₃ | CH₃ | H | H | H | 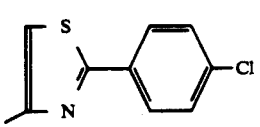 | H |
| CH₃ | OCH₃ | CH₃ | H | H | H | 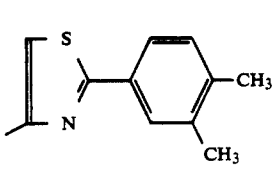 | H |
| CH₃ | OCH₃ | Cl | H | H | H | 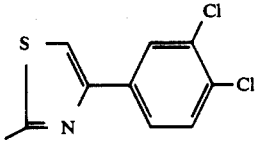 | H |
| CH₃ | OCH₃ | H | CH₃ | H | H | 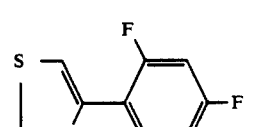 | H |
| CH₃ | OCH₃ | H | CH₃ | H | H | 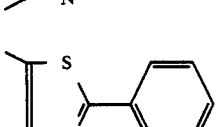 | H |
| CH₃ | OCH₃ | H | H | H | H | 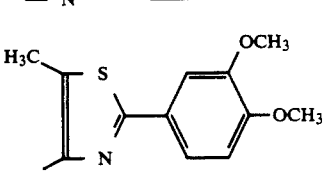 | H |
| CH₃ | OCH₃ | H | H | H | H | 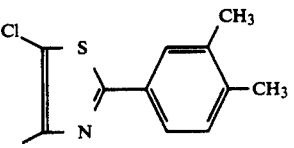 | H |
| CH₃ | OCH₃ | H | H | H | H | 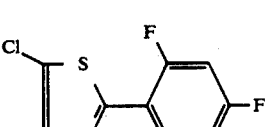 | H |
| CH₃ | OCH₃ | H | H | H | H | 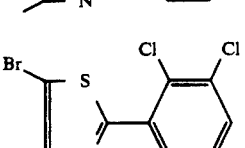 | H |

TABLE 1-continued
| R¹ | R² | R³ | R⁴ | R⁵ | R⁶ | R⁷ | R⁸ |
|----|----|----|----|----|----|----|----|
| CH₃ | OCH₃ | H | H | H | H | 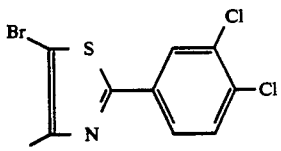 | H |
| CH₃ | OCH₃ | H | H | H | H | 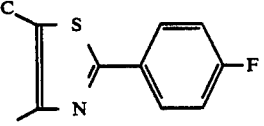 | H |
| CH₃ | OCH₃ | H | H | H | H | 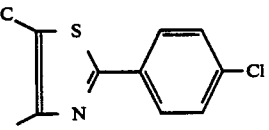 | H |
| CH₃ | OCH₃ | H | H | H | H | 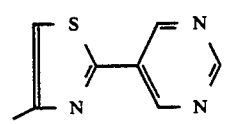 | H |
| CH₃ | OCH₃ | H | H | H | H | 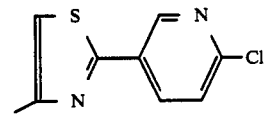 | H |
| CH₃ | OCH₃ | H | H | H | H | 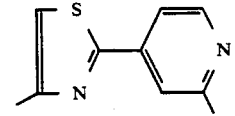 | H |
| CH₃ | OCH₃ | H | H | H | H | 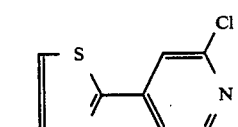 | H |
| CH₃ | OCH₃ | H | H | H | H | 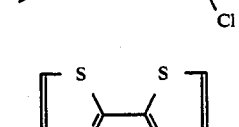 | H |
| CH₃ | OCH₃ | H | H | H | H |  | H |
| CH₃ | OCH₃ | H | H | H | H | 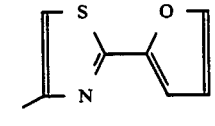 | H |
| CH₃ | OCH₃ | H | H | H | H | 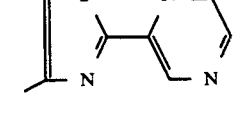 | H |

TABLE 1-continued

| R¹ | R² | R³ | R⁴ | R⁵ | R⁶ | R⁷ | R⁸ |
|---|---|---|---|---|---|---|---|
| CH₃ | OCH₃ | H | H | H | H | (structure: thiazole linked to thiazole with phenyl) | H |
| CH₃ | OCH₃ | H | H | H | H | (structure: thiazole with C(CH₃)=N-O-N=C(CH₃)) | H |
| CH₃ | OCH₃ | H | H | H | H | (structure: thiazole linked to N-phenyl pyrazole) | H |
| CH₃ | OCH₃ | H | H | H | H | (structure: Br-thiazole linked to 2-methoxypyridine) | H |
| CH₃ | OCH₃ | H | H | H | H | (structure: thiazole linked to 2-methylthiopyridine) | H |
| CH₃ | OCH₃ | H | H | H | H | (structure: thiazole linked to N-methyl pyrrole) | H |
| CH₃ | OCH₃ | H | H | H | H | (structure: Br-thiazole linked to C(C₂H₅)(CH₃)(C₂H₅)) | H |
| CH₃ | OCH₃ | H | H | H | H | (structure: Cl-thiazole linked to Cl-thiazole with phenyl) | H |

TABLE 1-continued

| R¹ | R² | R³ | R⁴ | R⁵ | R⁶ | R⁷ | R⁸ |
|---|---|---|---|---|---|---|---|
| CH₃ | OCH₃ | H | H | H | H | (thiazoline with 3,4-dichlorophenyl) | H |
| CH₃ | OCH₃ | H | H | H | H | (thiazoline with 3,4,5-trimethoxyphenyl) | H |
| CH₃ | OCH₃ | H | H | H | H | (thiazoline with 3,4,5-trichlorophenyl) | H |
| CH₃ | OCH₃ | H | H | H | H | (thiazoline with 2,4,6-trimethylphenyl) | H |
| CH₃ | OCH₃ | H | H | H | H | (thiazoline with 4-ethylphenyl) | H |
| CH₃ | OCH₃ | H | H | H | H | (thiazoline with C(CH₃)₃) | H |
| CH₃ | OCH₃ | H | H | H | H | (thiazoline with CH₂-phenyl) | H |
| CH₃ | OCH₃ | H | H | H | H | (thiazoline with CH₂-(4-chlorophenyl)) | H |
| CH₃ | OCH₃ | H | H | H | H | (thiazoline with (CH₂)₄—CH₃) | H |
| CH₃ | OCH₃ | H | H | H | H | (chloro-thiazoline with phenyl) | H |

TABLE 1-continued
| R¹ | R² | R³ | R⁴ | R⁵ | R⁶ | R⁷ | R⁸ |
|---|---|---|---|---|---|---|---|
| CH₃ | OCH₃ | H | H | H | H | 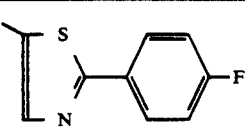 | H |
| CH₃ | OCH₃ | H | H | H | H | 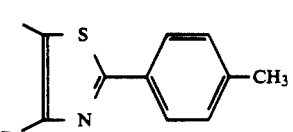 | H |
| CH₃ | OCH₃ | H | H | H | H | 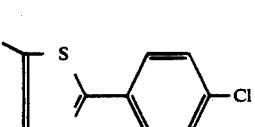 | H |
| CH₃ | OCH₃ | H | H | H | H | 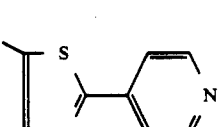 | H |
| CH₃ | OCH₃ | H | H | H | H | 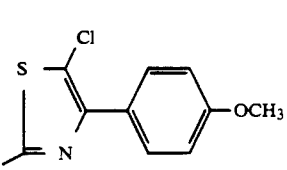 | H |
| CH₃ | OCH₃ | H | H | H | H | 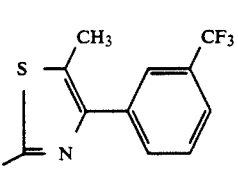 | H |
| CH₃ | OCH₃ | H | H | H | H | 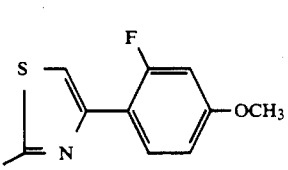 | H |
| CH₃ | OCH₃ | H | H | H | H | 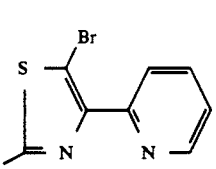 | H |
| CH₃ | OCH₃ | H | H | H | H | 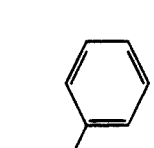 | H |
| CH₃ | OCH₃ | H | H | H | H | 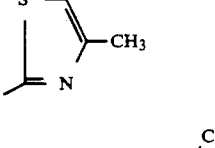 | H |

TABLE 1-continued

| R¹ | R² | R³ | R⁴ | R⁵ | R⁶ | R⁷ | R⁸ |
|---|---|---|---|---|---|---|---|
| CH₃ | OCH₃ | H | H | H | H | thiazole-pyrimidine group | H |
| CH₃ | OCH₃ | H | H | H | H | 2-phenylthiazol-4-yl | H |
| CH₃ | OCH₃ | H | H | H | H | 2-(4-chlorophenyl)thiazol-4-yl | H |
| CH₃ | OCH₃ | H | H | H | H | 2-(3,4-dichlorophenyl)thiazol-4-yl | H |
| CH₃ | OCH₃ | H | H | H | H | 2-(4-fluorophenyl)thiazol-4-yl | H |
| CH₃ | OCH₃ | H | H | H | H | 5-bromo-4-(4-chlorophenyl)thiazol-2-yl derivative | H |
| CH₃ | OCH₃ | H | H | H | H | 2-(3-chloro-4-methoxyphenyl)thiazol-4-yl | H |
| CH₃ | OCH₃ | H | H | H | H | 2-(thiophen-2-yl)thiazol-4-yl | H |

TABLE 1-continued

| R¹ | R² | R³ | R⁴ | R⁵ | R⁶ | R⁷ | R⁸ |
|----|----|----|----|----|----|----|----|
| CH₃ | OCH₃ | H | H | H | H | 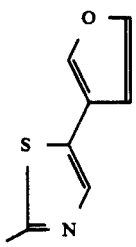 | H |
| CH₃ | OCH₃ | H | H | H | H | 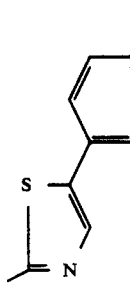 | H |
| CH₃ | OCH₃ | H | H | H | H | 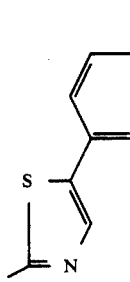 | H |
| CH₃ | OCH₃ | H | H | H | H | 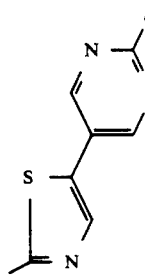 | H |

If, for example, methyl 3-hydroxy-2-[6-[2-(2,4-difluorophenyl)thiazol-4-yl]-indol-1-yl]-acrylate and dimethyl sulphate are used as starting substances, the course of the reaction of process (b) according to the invention may be represented by the following equation:

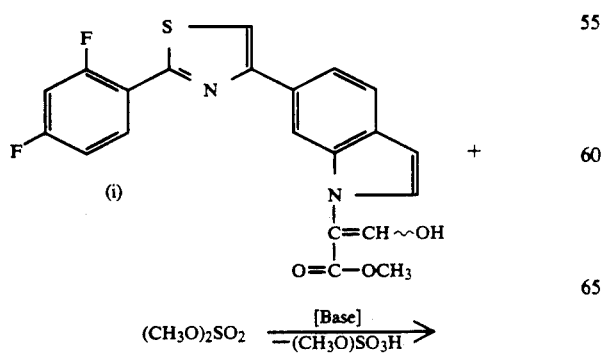

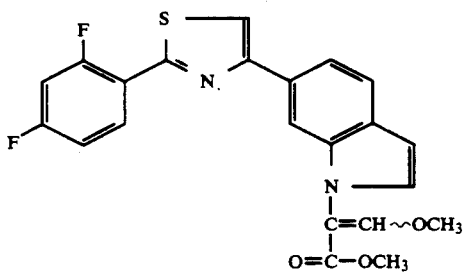

If, for example, methyl [6-[2-(phenyl)-thiazol-4-yl]-3-methylindol-1-yl]-acetate and dimethylformamide dimethyl acetal are used as starting substances, the course of the reaction of process (b) according to the invention may be represented by the following equation:

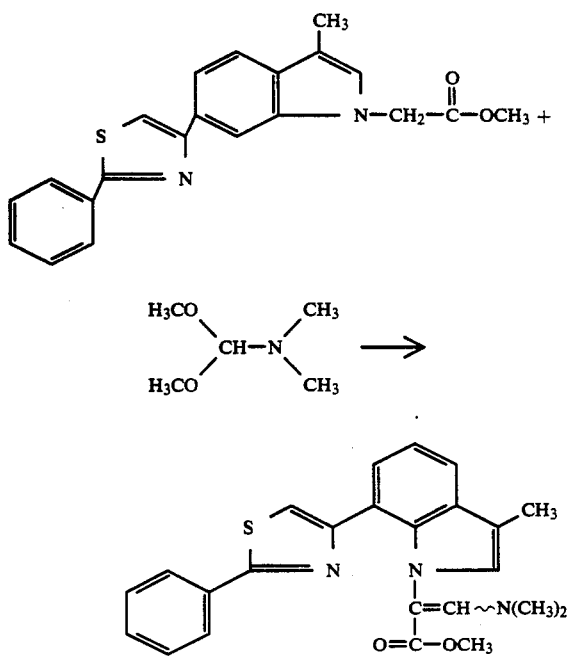

If, for example, methyl 2-oxo-[6-[2-(pyridin-4-yl)-thiazol-4-yl]-3-chloroindol-1-yl]-acetate and [(methylthio)-(trimethylsilyl)]methylene-lithium are used as starting compounds, the course of the reaction of process (c) according to the invention may be represented by the following equation:

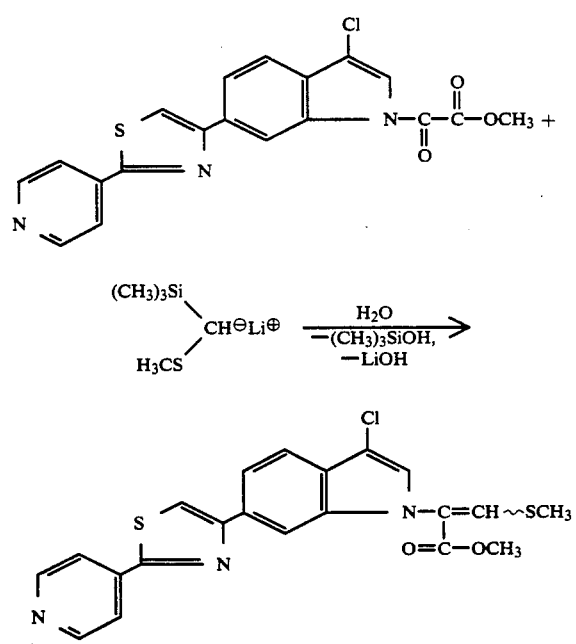

If, for example, methyl 2-[6-[5-bromo-2-(pyridin-2-yl)-thiazol-4-yl]-indol-1-yl]-3-methanesulphonyloxyacrylate and methylmercaptan are used as starting substances, the course of the reaction of process (d) according to the invention may be represented by the following equation:

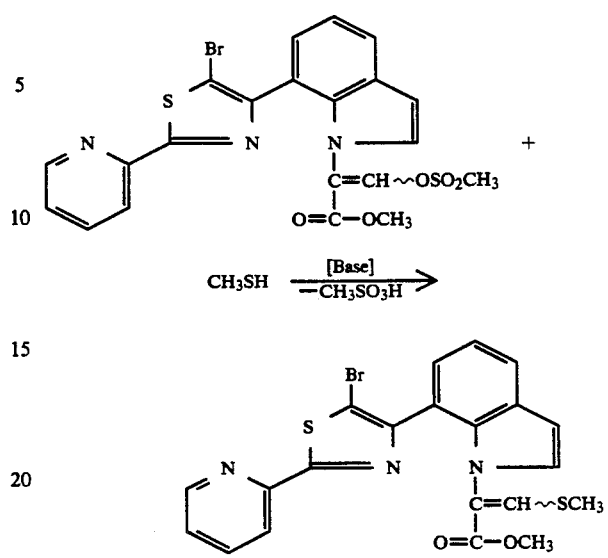

Formula (II) provides a general definition of the hydroxyacrylic esters or alkali metal salts thereof required as starting substances for carrying out process (a) according to the invention. In this formula (II), $R^1$, $R^3$, $R^4$, $R^5$, $R^6$, $R^7$ and $R^8$ preferably represent those radicals which have already been mentioned in connection with the description of the substances of the formula (I) according to the invention as being preferred for these substituents.

M preferably represents hydrogen, or represents a lithium, sodium or potassium cation.

The hydroxyacrylic esters of the formula (II) which are required for carrying out process (a) according to the invention were hitherto unknown and are a subject of the invention.

They are obtained when substituted acetic esters of the formula (IV)

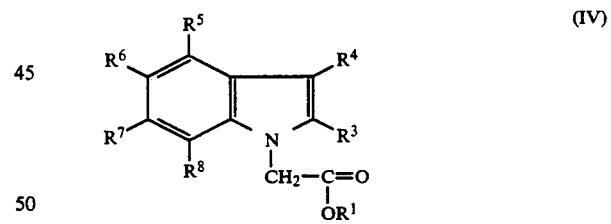

in which $R^1$, $R^3$, $R^4$, $R^5$, $R^6$, $R^7$ and $R^8$ have the abovementioned meanings, are reacted with formic esters of the formula (X)

in which $R^{14}$ represents alkyl, in particular methyl or ethyl, if appropriate in the presence of a diluent, such as, for example, dimethylformamide, and if appropriate in the presence of a basic reaction auxiliary, such as, for example, sodium hydride, at temperatures of from $-20°$ C. to $+50°$ C. (cf., for example, European Patent 274,825).

Formic esters of the formula (X) are generally known compounds of organic chemistry.

Formula (III) provides a general definition of the alkylating agents furthermore required as starting substances for carrying out process (a) according to the invention. In this formula (III), $R^{11}$ preferably represents those radicals which have already been mentioned in connection with the description of the substances of the formula (I) according to the invention as being preferred for this substituent.

$E^1$ represents a leaving group customary in alkylating agents, preferably an optionally substituted alkyl-, alkoxy-, or arylsulphonyloxy radical, such as, for example, a methoxysulphonyloxy radical, an ethoxysulphonyloxy radical or a p-toluenesulphonyloxy radical, or represents halogen, in particular, chlorine, bromine or iodine.

The alkylating agents of the formula (III) are generally known compounds of organic chemistry.

The substituted acetic esters of the general formula (IV) which are required as starting substances for carrying out process (b) according to the invention and for the synthesis of the precursors of the formula (II) are new and a subject of the invention. In this formula (IV), $R^1$, $R^3$, $R^4$, $R^5$, $R^6$, $R^7$ and $R^8$ preferably represent those radicals which have already been mentioned in connection with the description of the substances of the formula (I) according to the invention as being preferred for these substituents.

The compounds of the formula (IV) are obtained when indole derivatives of the general formula (XI)

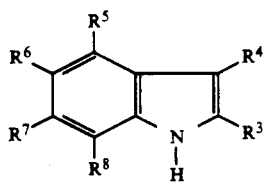

(XI)

in which $R^3$, $R^4$, $R^5$, $R^6$, $R^7$ and $R^8$ have the abovementioned meanings, are reacted with acetic acid derivatives of the general formula (XII)

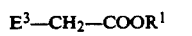

(XII)

in which
  $R^1$ has the abovementioned meaning and
  $E^3$ represents an electron-attracting leaving group, preferably halogen, in particular chlorine or bromine, if appropriate in the presence of a diluent, such as, for example, acetonitrile or acetone, and if appropriate in the presence of a basic auxiliary, such as, for example, potassium carbonate or potassium tert.-butylate, at temperatures between $-20°$ C. and $+100°$ C.

The acetic acid derivatives of the formula (XII) are generally known compounds of organic chemistry.

The indole derivatives of the general formula (XI) were hitherto unknown and are a subject of the invention. However, they are obtained by known processes in an analogous manner, for example by reacting nitrobenzene derivatives of the formula (XIII)

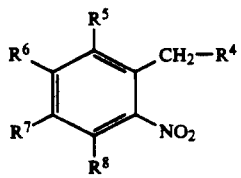

(XIII)

in which $R^4$, $R^5$, $R^6$, $R^7$ and $R^8$ have the abovementioned meanings, with compounds of the formula (XIV)

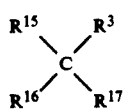

(XIV)

in which
  $R^3$ has the abovementioned meaning,
  $R^{15}$ represents alkoxy or dialkylamino,
  $R^{16}$ represents alkoxy or dialkylamino, and
  $R^{17}$ represents dialkylamino, if appropriate in the presence of a diluent, such as, for example, toluene or dimethylformamide, at temperatures between $25°$ C. and $200°$ C. and if appropriate under a pressure of from 1 to 100 bar, to give the compounds of the general formula (XV)

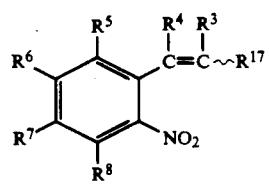

(XV)

in which $R^3$ $R^4$, $R^5$, $R^6$, $R^7$, $R^8$ and $R^{17}$ have the abovementioned meanings, and cyclizing the resulting compounds of the formula (XV), if appropriate after they have been isolated and/or purified, if appropriate in the presence of a diluent, such as, for example, methanol, ethanol, tetrahydrofuran or dioxane, if appropriate in the presence of an inert gas, such as, for example, nitrogen, using customary reducing agents, such as, for example, hydrogen, in the presence of a suitable catalyst, such as, for example, Raney nickel, and at a pressure of between 1 and 200 bar and at temperatures and between $-20°$ C. and $+200°$.

The compounds of the general formula (XIV) are generally known compounds of organic chemistry (cf. Tetrahedron 35, 1675 (1979)).

The nitrobenzene derivatives of the formula (XIII)

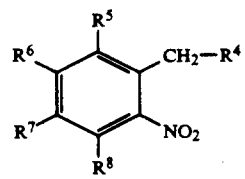

(XIII)

in which $R^4$, $R^5$, $R^6$, $R^7$ and $R^8$ have the abovementioned meanings, are new with the exception of the compounds 5-chloro-4-(iodomethyl)-2-(4-methyl-3-nitrophenyl)-thiazole; 4-(iodomethyl)-2-(4-methyl-3-nitrophenyl)-thiazole; 5-chloro-4-(chloromethyl)-2-(4- methyl-3-nitrophenyl)thiazole; 4-(chloromethyl)-2-(4-methyl-3-nitrophenyl)-5-nitrothiazole; 5-bromo-4-(chloromethyl)-2-(4-methyl-3-nitrophenyl)-thiazole; 4-(chloromethyl)-2-(4-methyl-3-nitrophenyl)-thiazole; 5-bromo-N,N-dimethyl-4-(4-methyl-3-nitrophenyl)-2-thiazolamine and 5-methyl-2-(p-nitrophenyl)-4-(3-nitro-p-tolyl)-thiazole (cf. *Rev. Roum. Chim.* 28 (6), 645-51, 1983; *Acta Chim. Acad. Sci. Hung.* 83 (3-4), 381-9, 1974; DE-OS (German Published Specification) 2,130,981 and Rev. Roum. Chim. 12(7), 905-11).

The nitrobenzene derivatives of the formula (XIII) are obtained by one of the processes described below:

a) Nitrobenzene derivatives of the general formula (XIIIa)

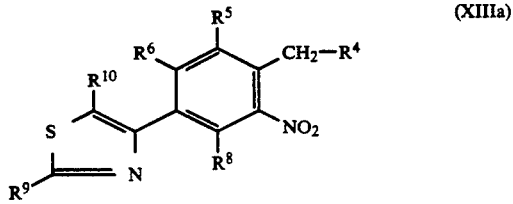

in which $R^4$, $R^5$, $R^6$, $R^8$, $R^9$ and $R^{10}$ have the abovementioned meanings, are obtained when compounds of the formula (XVI)

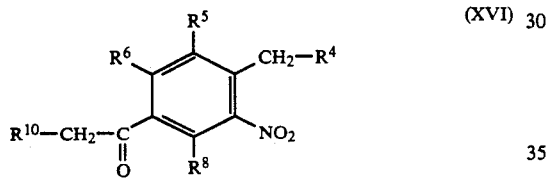

in which $R^4$, $R^5$, $R^6$, $R^8$ and $R^{10}$ have the abovementioned meanings, are brominated with bromine, if appropriate in the presence of a diluent, such as, for example, glacial acetic acid or dichloromethane, at temperatures between 0° C. and 100° C., to give the compounds of the formula (XVII)

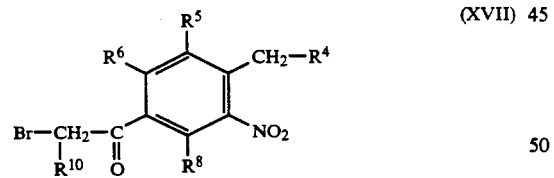

in which $R^4$, $R^5$, $R^6$, $R^8$ and $R^{10}$ have the abovementioned meanings, and the compounds of the formula (XVII) are subsequently cyclized with thioamides of the formula (XVIII)

in which $R^9$ has the abovementioned meaning, if appropriate in the presence of a diluent, such as, for example, ethanol, at temperatures between $-20°$ C. and $+120°$ C., or b) nitrobenzene derivatives of the general formula (XIIIb)

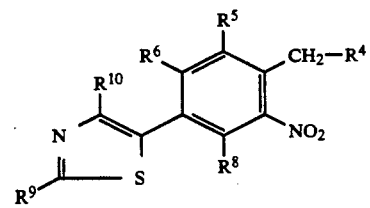

in which $R^4$, $R^5$, $R^6$, $R^8$, $R^9$ and $R^{10}$ have the abovementioned meanings, are obtained when compounds of the formula (XIX)

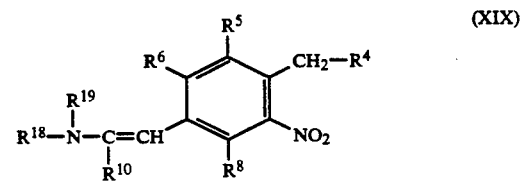

in which
$R^4$, $R^5$, $R^6$, $R^8$ and $R^{10}$ have the abovementioned meanings and
$R^{18}$ and $R^{19}$ in each case independently of one another represent straight-chain or branched alkyl having 1 to 4 carbon atoms, or together represent a straight-chain or branched saturated alkylene chain having 4 to 8 carbon atoms which is optionally interrupted by one or 2 hetero atoms from the series comprising oxygen, sulphur or nitrogen, but preferably represents dimethylamino, pyrrolidinyl, piperidinyl or morpholinyl, are brominated with bromine, if appropriate in the presence of a diluent, such as, for example, dichloromethane, at temperatures between $-80°$ C. and $+100°$ C. to give the compounds of the formula (XX)

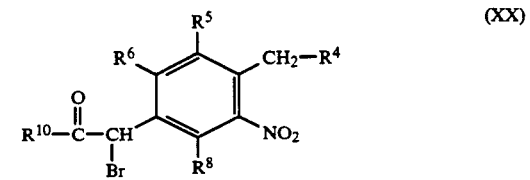

in which $R^4$, $R^5$, $R^6$, $R^8$ and $R^{18}$ have the abovementioned meanings, and the compounds of the formula (XX) are subsequently cyclized with thioamides of the formula (XVIII)

in which $R^9$ has the abovementioned meaning, if appropriate in the presence of a diluent, such as, for example, ethanol, at temperatures between $-20°$ C. and $+120°$ C., or c) nitrobenzene derivatives of the general formula (XIIIc-1)

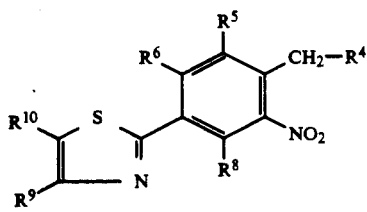 (XIIIc-1)

in which $R^4$, $R^5$, $R^6$, $R^8$, $R^9$ and $R^{10}$ have the abovementioned meanings, or

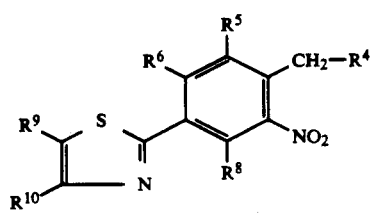 (XIIIc-2)

in which $R^4$, $R^5$, $R^6$, $R^8$, $R^9$ and $R^{10}$ have the abovementioned meanings, are obtained when thioamides of the formula (XXI)

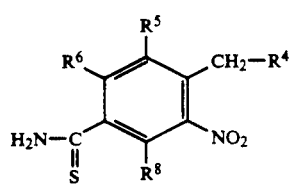 (XXI)

in which $R^4$, $R^5$, $R^6$ and $R^8$ have the abovementioned meanings, are reacted with ketones of the formula (XXIIa)

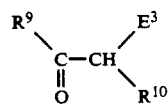 (XXIIa)

in which $R^9$, $R^{10}$ and $E^3$ have the abovementioned meanings, or with ketones of the formula (XXIIb)

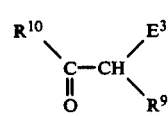 (XXIIb)

in which $R^9$, $R^{10}$ and $E^3$ have the abovementioned meanings, if appropriate in the presence of a diluent, such as, for example, methanol, ethanol or n-propanol, and if appropriate in the presence of a basic reaction auxiliary, such as, for example, pyridine or potassium carbonate, at temperatures between $-25°$ C. and $+120°$ C.

The thioamides of the formula (XXI) are new. However, they are obtained by known processes in an analogous manner, for example when nitriles of the formula (XXIII)

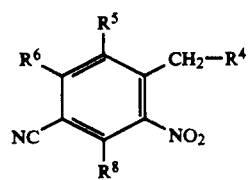 (XXIII)

in which $R^4$, $R^5$, $R^6$ and $R^8$ have the abovementioned meanings,

α) are reacted either in customary fashion with carbon disulphide, if appropriate in the presence of a diluent, such as, for example, toluene, pyridine or dimethylformamide, and if appropriate in the presence of a protective gas atmosphere, such as, for example, hydrogen, at temperatures between 25° C. and 100° C. (cf. Organikum, Organisch-Chemisches Grundpraktikum, [Basic Laboratory Practical in Organic Chemistry], VEB Deutscher Verlag der Wissenschaften 1986, 424), or β) are reacted with hydrogen sulphide, if appropriate in the presence of a diluent, such as, for example, pyridine and/or triethylamine, and if appropriate using a protective gas atmosphere, such as, for example, nitrogen or argon, at temperatures between 0° C. and 120° C., or γ) are hydrolyzed with concentrated inorganic acids, such as, for example, sulphuric acid, at room temperature, if appropriate in the presence of diluents, such as, for example, dioxane, methanol or ethanol, or from mixtures of these solvents with water at temperatures between 25° C. and 100° C., or without a diluent to give the amides of the formula (XXIV)

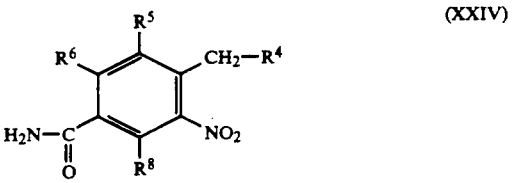 (XXIV)

in which $R^4$, $R^5$, $R^6$ and $R^8$ have the abovementioned meanings, (cf. Organikum, Organisch-Chemisches Grundpraktikum, [Basic Laboratory Practical in Organic Chemistry], VEB Deutscher Verlag der Wissenschaften 1986, 424) and the resulting compounds of the formula (XXIV) are reacted with "Lawesson's reagent" of the formula (XXV)

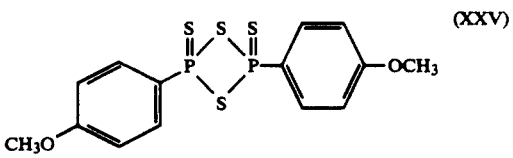 (XXV)

if appropriate in the presence of a diluent, such as, for example, toluene, xylene or dioxane, at temperatures between 20° C. and 150° C.

The compounds of the formula (XXIII) and (XXV) are generally known compounds of organic chemistry.

In some cases, it can be advantageous to react the nitrobenzene derivatives of the formula (XIIIa), (XIIIb), (XIIIc-1) and (XIIIc-2), in which $R^{10}$ represents hydrogen, with suitable reactants, such as, for example, halogenating agents or nitrating agents, by generally known customary methods of organic chemistry, to give the compounds of the general formula (XIII) and, if appropriate, to form derivatives by further suitable reactions.

The compounds of the formula (XVI), (XVIII), (XIX), (XXIIa) and (XXIIb) are generally known compounds of organic chemistry.

Formulae (Va) and (Vb) provide general definitions of the formamides and derivatives thereof furthermore required as starring substances for carrying out process (b) according to the invention. In these formulae (Va) and (Vb), $R^{2-2}$ preferably represents dialkylamino having in each case 1 to 6, in particular 1 to 4, carbon atoms in the individual straight-chain or branched alkyl moieties. $R^{2-2}$ very particularly preferably represents dimethylamino or diethylamino.

$R^{12}$ and $R^{13}$ independently of one another preferably represent in each case straight-chain or branched alkoxy having 1 to 4 carbon atoms, in particular methoxy or ethoxy, or a dialkylamino radical having in each case 1 to 6, in particular 1 to 4, carbon atoms in the individual straight-chain or branched alkyl moieties.

The formamides of the formula (Va) and their derivatives of the formula (Vb) are generally known compounds of organic chemistry.

Formula (VI) provides a general definition of the ketocarboxylic acid derivatives required as starting substances for carrying out process (c) according to the invention.

In this formula (VI), $R^1$, $R^3$, $R^4$, $R^5$, $R^6$, $R^7$ and $R^8$ preferably represent those radicals which have already been mentioned in connection with the description of the substances of the formula (I) according to the invention as being preferred for these substituents.

The ketocarboxylic acid derivatives of, the formula (VI) are new and a subject of the invention. However, they are obtained in analogy to known processes, for example by reacting oxalic esters of the formula (XXVI)

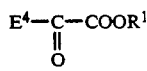  (XXVI)

in which
$R^1$ has the abovementioned meaning and
$E^4$ represents alkoxy or halogen, in particular methoxy, ethoxy or chlorine,
with indole derivatives of the formula (XI)

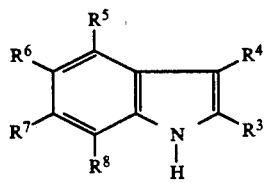  (XI)

in which $R^3$, $R^4$, $R^5$, $R^6$, $R^7$ and $R^8$ have the abovementioned meanings, if appropriate in the presence of a diluent, such as, for example, dichloromethane or tetrahydrofuran, and if appropriate in the presence of a base, such as, for example, n-butyllithium, sodium hydride, potassium t-butylate, triethylamine or pyridine at temperatures between $-80°$ C. and $+80°$ C. (cf. DE-OS (German Published Specification) 3,807,232).

Formula (VII) provides a general definition of the organometal compounds furthermore required as starting substances for carrying out process (c) according to the invention. In this formula (VII), $R^{2-3}$ preferably represents those radicals which have already been mentioned in connection with the description of the substances of the formula (I) according to the invention as being preferred for this substituent.

The organometal compounds of the formula (VII) are known (cf., for example, J. Org. Chem. 33, 780 [1968]; J. Org. Chem. 37, 939 [1972]).

Formula (VIII) provides a general definition of the substituted acrylic esters required as starting substances for carrying out process (d) according to the invention. In this formula (VIII), $R^1$, $R^3$, $R^4$, $R^5$, $R^6$, $R^7$ and $R^8$ preferably represent those radicals which have already been mentioned in connection with the description of the substances of the formula (I) according to the invention as being preferred for these substituents.

$E^2$ preferably represents a suitable acyloxy or sulphonyloxy radical, in particular an acetoxy, a methanesulphonyloxy or a p-toluenesulphonyloxy radical.

The substituted acrylic esters of the formula (VIII) were hitherto unknown.

They are obtained when hydroxyacrylic esters of the formula (II)

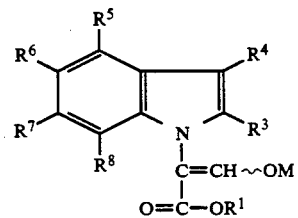  (II)

in which M, $R^1$, $R^3$, $R^4$, $R^5$, $R^6$, $R^7$ and $R^8$ have the abovementioned meanings are reacted with acid chlorides of the formula (XXVII)

  (XXVII)

in which $R^{20}$ represents an acyl or sulphonyl radical, in particular an acetyl, a methanesulphonyl or a p-toluenesulphonyl radical,
if appropriate in the presence of a diluent, such as, for example, dichloromethane, and if appropriate in the presence of an acid-binding agent, such as, for example, triethylamine or pyridine, at temperatures of from $-20°$ C. to $+120°$ C.

Acid chlorides of the formula (XXVII) are generally known compounds of organic chemistry.

Formula (IX) provides a general definition of the thiols furthermore required as starting substances for carrying out process (d) according to the invention. In this formula (IX), $R^{2-3}$ preferably represents those radicals which have already been mentioned in connection with the description of the substances of the formula (I) according to the invention as being preferred for this substituent.

The thiols of the formula (IX) are generally known compounds of organic chemistry.

Suitable diluents for carrying out process (a) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or sulphoxides, such as dimethylsulphoxide.

If appropriate, process (a) according to the invention can also be carried out in a two-phase system, such as, for example, water/toluene or water/dichloromethane, if appropriate in the presence of a phasetransfer catalyst. The following may be mentioned as examples of such catalysts: tetrabutylammonium iodide, tetrabutylammonium bromide, tributyl-methylphosphonium bromide, trimethyl-$C_{13}$/-$C_{15}$-alkylammonium chloride, dibenzyl-dimethyl-ammonium methylsulphate, dimethyl-$C_{12}$/$C_{14}$-alkyl-benzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Process (a) according to the invention is preferably carried in the presence of a suitable basic reaction auxiliary. Suitable reaction auxiliaries are all inorganic and organic bases which can customarily be used. The following are preferably used: alkali metal hydrides, alkali metal hydroxides, alkali metal amides, alkali metal alcoholates, alkali metal carbonates or alkali metal hydrogen carbonates, such as, for example, sodium hydride, sodium amide, sodium hydroxide, sodium methylate, sodium ethylate, potassium t-butylate, sodium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the process is carried out at temperatures of from $-30°$ C. to $+120°$ C., preferably at temperatures of from $-20°$ C. to $+60°$ C.

For carrying out process (a) according to the invention, 1.0 to 10.0 moles, preferably 1.0 to 5.0 moles, of alkylating agent of the formula (III) and if appropriate 1.0 to 5.0 moles, preferably 1.0 to 2.0 moles, of reaction auxiliary are generally employed per mole of 3-hydroxyacrylic ester or of a corresponding alkali metal salt of the formula (II). It is also possible in this connection to prepare the 3-hydroxyacrylic esters of their alkali metal salts of the formula (II) required as starting compounds for carrying out process (a) according to the invention in a previous reaction directly in the reaction vessel and to react further with the alkylating agent of the formula (III) according to process (a) according to the invention directly from the reaction mixture, without isolation ("one-pot process"). The reaction is carried out and the reaction products are worked up and isolated by generally customary methods (cf. also the Preparation Examples).

Suitable diluents for carrying out process (b) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, or ethers, such as diethyl ether, dioxane, tetrahydrofuran or ethylene glycol dimethyl ether or ethylene glycol diethyl ether.

However, it is also possible to carry out process (b) according to the invention without adding diluent.

When carrying out process (b) according to the invention, the reaction temperatures can be varied within a substantial range. In general, the process is carried out at temperatures of from $-20°$ C. to $+200°$ C., preferably at temperatures of from $0°$ C. to $150°$ C.

For carrying out process (b) according to the invention, 1.0 to 30.0 moles, preferably 1.0 to 15.0 moles, of formamide of the formula (Va) or of a corresponding derivative of the formula (Vb) are generally employed per mole of substituted acetic ester of the formula (IV).

The reaction is carried out and the reaction products are worked up and isolated by generally customary methods (cf. in this context also G. Mathieu; J. Weill-Raynal .Formation of C-C-Bonds., Vol. I; p. 229-244; Thieme Verlag Stuttgart 1973).

Suitable diluents for carrying out process (c) according to the invention are inert organic solvents. These include, in particular, aliphatic, alicyclic or aromatic hydrocarbons, such as, for example, benzine, toluene, xylene, petroleum ether, hexane or cyclohexane, or ethers, such as diethyl ether, dioxane, tetrahydrofuran or ethylene glycol dimethyl ether or ethylene glycol diethyl ether.

When carrying out process (c) according to the invention, the reaction temperatures can be varied within a substantial range. In general, the process is carried out at temperatures of from $-100°$ C. to $+100°$ C., preferably at temperatures of from $-80°$ C. to $+50°$ C.

For carrying out process (c) according to the invention, 1.0 to 1.5 moles, preferably 1.0 to 1.2 moles, of an organometal compound of the formula (VII) are generally employed per mole of ketocarboxylic acid derivative of the formula (VI). The reaction is carried out and the reaction products are worked and isolated by known processes (cf., for example, *J. Org. Chem.* 33, 780 [1968]; *J. Org. Chem.* 37, 939 [1972]).

Suitable diluents for carrying out process (d) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (d) is preferably carried out in the presence of a suitable reaction auxiliary. Suitable reaction auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, or tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (d) according to the invention, the reaction temperatures can be varied within a substantial range. In general, the process is carried out at temperatures of from −20° C. to 180° C., preferably at temperatures of from 0° C. to 150° C.

If appropriate, the process according to the invention can also be carried out under pressure, depending on the boiling point of the reactants used, for example, when low-boiling thiols of the formula (IX) are used.

In this case, it is preferred to carry out the process at the pressure which is established when the mixture is heated to the reaction temperature required under the reaction conditions.

For carrying out process (d) according to the invention, 1.0 to 20.0 moles, preferably 1.0 to 5.0 moles, of thiol of the formula (IX) and if appropriate 1.0 to 5.0 moles, preferably 1.0 to 1.5 moles of reaction auxiliary are generally employed per mole of substituted acrylic ester of the formula (VIII). The reaction is carried out and the reaction products are worked up and isolated by generally customary methods.

The active compounds of the formulae (I) and (IV) according to the invention have a powerful action against pests and can be employed in practice for combating undesired harmful organisms. The active compounds are suitable for use as plant protection agents) in particular as fungicides and insecticides.

Fungicidal agents in plant protection are employed for combating Plasmodiophoromycetes, Oomycetes, Chytridiomycetes, Zygomycetes, Aacomycetes, Basidiomycetes and Deuteromycetes.

Some causative organisms of fungal diseases which come under the generic names listed above may be mentioned as examples, but not by way of limitation:
Pythium species, such as, for example, *Pythium ultimum;* Phytophthora species, such as, for example, *Phytophthora infestans;*
  Pseudoperonospora species, such as, for example, *Pseudoperonospora humuli* or *Pseudoperonospora cubensis;*
  Plasmopara species, such as, for example, *Plasmopara viticola;* .
  Peronospora species, such as, for example, *Peronospora pisi* or *P. brassicae;*
  Erysiphe species, such as, for example, *Erysiphe graminis;*
  Sphaerotheca species, such as, for example, *Sphaerotheca fuliginea;*
  Podosphaera species, such as, for example, *Podosphaera leucotricha;*
  Venturia species, such as, for example, *Venturia inaequalis;*
  Pyrenophora species, such as, for example, *Pyrenophora teres* or *P. graminea* (conidia form: Drechslera, syn: Helminthosporium);
  Cochliobolus species, such as, for example, *Cochliobolus sativus* (conidia form: Drechslera, syn: Helminthosporium);
  Uromyces species, such as, for example, *Uromyces appendiculatus;*
  Puccinia species, such as, for example, *Puccinia recondita;*
  Tilletia species, such as, for example, *Tilletia caries;*
  Ustilago species, such as, for example, *Ustilago nuda* or *Ustilago avenae;*
  Pellicularia species, such as, for example, *Pellicularia sasakii;*
  Pyricularia species, such as, for example, *Pyricularia oryzae;*
  Fusarium species, such as, for example, *Fusarium culmorum;*
  Botrytis species, such as, for example, *Botrytis cinerea;*
  Septoria species, such as, for example, *Septoria nodorum;*
  Leptosphaeria species, such as, for example, *Leptosphaeria nodorum;*
  Cercospora species, such as, for example, *Cercospora canescens;*
  Alternaria species, such as, for example, *Alternaria brassicae* and
  Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for protectively combating Venturia species on apples, Phytophthora species on tomatoes and *Cochliobolus sativus* and *Pyrenophora teres* species on barley, and for protectively combating rice diseases, such as, for example, against the pathogen causing rice blast disease (*Pyricularia oryzae*).

Moreover, the active compounds according to the invention also have a fungicidal action against Plasmopara, *Septoria nodorum, Cochliobolus sativus* and Fusariosen as well as against *Uncinula necator* on vine and *Venturia inaequalis, Erysiphe graminis,* Botrytis and Pellicularia and a broad and good in-vitro action.

Furthermore, the active compounds are suitable for combating animal pests, preferably arthropods and nematodes, in particular insects and arachnida encountered in agriculture, in forestry, in the protection of stored products and of materials, and in the hygiene field. They are active against normally sensitive and resistant species and against all or individual stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.*

From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp.

From the order of the Thysanoptera, for example, *Hercinothrips femoralis* and *Thrips tabaci.* From the order of the Heteroptera, for example, Eurygaster spp.,

*Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix turberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeuceus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Ambylomma spp., Hyalomma spp., Ixodes spp., Psoroptes spp., Chorioptes spp., Sarcoptes spp., Tarsonemus spp., *Bryobia praetiosa,* Panonychus spp., and Tetraanychus spp.

The phytoparasitic nematodes include Pratylenchus spp., *Radopholus similis, Ditylenchus dipsaci, Tylenchulus semipenetrans,* Heterodera spp., Globedera ssp., Meloidogyne spp., Aphelenchoides spp., Longidorus spp., Xiphinema spp. and Trichodorus spp.

The active compounds according to the invention are distinguished by an outstanding insecticidal activity, in particular when applied against beetle larvae, such as, for example, *Phaedon cochleariae, Plutella xylostella* and *Spodoptera frugiperda,* and also against aphids, such as, for example, *Myzus persicae.*

Depending on their specific physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore to formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides, and herbicides and in mixtures with fertilizers and growth regulators.

The active compounds can be applied as such, in the form of their formulations or the use forms prepared therefrom, such as ready-to-use solutions, suspensions, wettable powders, pastes, soluble powders, dusting agents and granules. They are used in a customary manner, for example by pouring, spraying, atomizing, scattering, dusting, foaming, brushing on etc. It is furthermore possible to apply the active compounds using the ultralow volume method, or to inject the active compound preparation, or the active compound itself, into the soil. It is also possible to treat the seeds of the plants.

In the treatment of parts of plants, the active compound concentrations in the use forms can be varied within a substantial range. They are generally between 1 and 0.0001% by weight, preferably between 0.5 and 0.001%.

In the treatment of seeds, amounts of active compound of 0.001 to 50 g per kilogram of seed, preferably 0.01 to 10 g, are generally required.

In the treatment of the soil, active compound concentrations of 0.00001 to 0.1% by weight, preferably of 0.0001 to 0.02%, are required at the site of action.

PREPARATION EXAMPLES

Example 1

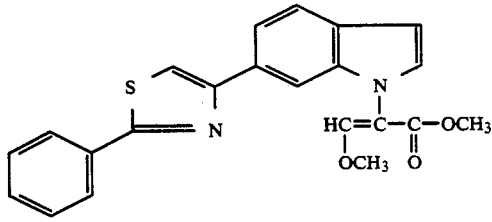

A solution of 6.10 g (17.51 mmol) of methyl [6-(2-phenyl-thiazol-4-yl)-indol-1-yl]-acetate in a mixture of 10 ml of dimethylformamide and 20 ml of methyl formate is added dropwise with stirring and cooling at a temperature of 0° C. to 5° C. to a suspension of 1.20 g (40.00 mmol) of sodium hydride (80% mixture with paraffin) in 10 ml of dimethylformamide. Stirring is continued at 0° C. for approximately 2 hours, and 6.00 g (47.57 mmol) of dimethyl sulphate are added dropwise at the same temperature and with vigorous stirring. Over 2 hours, the reaction mixture is now allowed to come to room temperature and then stirred with an excess of aqueous sodium hydrogen carbonate solution, the mixture is extracted with ethyl acetate, the combined extracts are dried over anhydrous sodium sulphate and filtered, and the filtrate is concentrated. The residue which remains is purified by column chromatography on silica gel (eluent: dichloromethane/n-hexane 2:1).

Methyl 3-methoxy-2-[6-(2-phenyl-thiazol-4-yl)-indol-1-yl]-acrylate is obtained as the Z-isomer of melting point m.p.: 145°-146° C., yield 2.20 g (32.1% of theory) and a Z/E isomer mixture (1:3), yield 1.50 g (21.9% of theory) of melting point m.p.: 150°-154° C.

Example 2

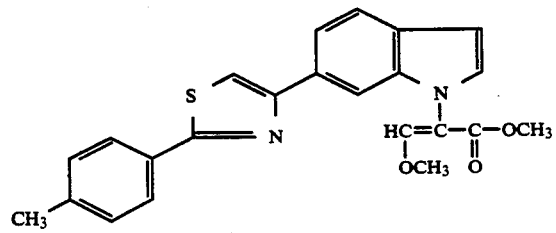

In an analogous manner to Example 1, methyl 3-methoxy-2-[6-[(4-methylphenyl)-thiazol-4-yl]-indol-1-yl]acrylate is obtained as the Z isomer: yield 2.90 g (42.6% of theory) of melting point m.p.: 145°-146° C. and a Z/E isomer mixture (7:93): yield 0.90 g (13.2% of theory) of melting point m.p.: 154°-155° C.

EXAMPLE 3

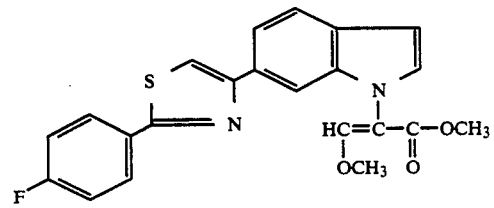

In an analogous manner to Examples 1 and 2, methyl 3-methoxy-2-[6-[(4-fluorophenyl)-thiazol-4-yl]indol-1-yl]-acrylate of melting point m.p.: 130°-131° C. is obtained.

The compounds of the formula (I)

(I)

$$\begin{array}{c}\text{structure}\end{array}$$

shown in the following Table 2 can be prepared analogously to Examples 1 to 3 and in accordance with the general information on the process.

TABLE 2

| Example No. | $R^1$ | $R^2$ | $R^3$ | $R^4$ | $R^5$ | $R^6$ | $R^7$ | $R^8$ | physical data |
|---|---|---|---|---|---|---|---|---|---|
| 4 | $CH_3$ | $OCH_3$ | H | H | H | H | 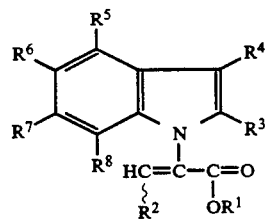 | H | m.p. 130° C. E/Z-mixture |

TABLE 2-continued

| Example No. | R¹ | R² | R³ | R⁴ | R⁵ | R⁶ | R⁷ | R⁸ | physical data |
|---|---|---|---|---|---|---|---|---|---|
| 5 | $CH_3$ | $N(CH_3)_2$ | H | H | H | H | 4-methoxyphenyl-thiazolyl | H | m.p. 42–43° C. |
| 6 | $CH_3$ | $OCH_3$ | H | H | H | H | 3,4-dichlorophenyl-thiazolyl | H | $n_D^{20}$ 1.5937 E/Z = 85/15 |
| 7 | $CH_3$ | $OCH_3$ | H | H | H | H | 3-chlorophenyl-thiazolyl | H | m.p. 44–45° C. E/Z = 50/50 |
| 8 | $CH_3$ | $OCH_3$ | H | H | H | H | 3-phenoxyphenyl-thiazolyl | H | $n_D^{20}$ 1.5863 E/Z = 60/40 |

PREPARATION OF THE STARTING COMPOUNDS

Example (IV-1)

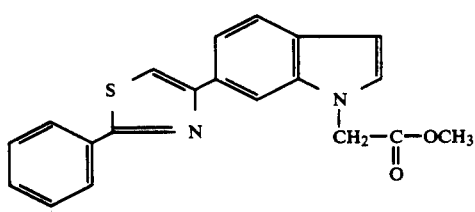

A mixture of 15.00 g (54.28 mmol) of 6-(2-phenyl-thiazol-4-yl)indole, 15.30 g (100.02 mmol) of methyl bromoacerate, 20 g of finely-ground potassium carbonate and 120 ml of acetonitrile is refluxed for 8 hours with stirring. The end of the reaction is determined by means of thin-layer chromatography. For working up, the mixture is allowed to cool, the contents of the reaction vessel are partitioned between water and ethyl acetate, and the organic phase is dried and concentrated. The residue which crystallizes is triturated with diisopropyl ether and filtered off with suction, and the solids are dried in a high vacuum at 50° C.

18.10 g (95.7% of theory) of methyl [6-(2-phenyl-thiazol-4-yl)-indol-1-yl]acetate of melting point 83° C. are obtained.

Example (IV-2)

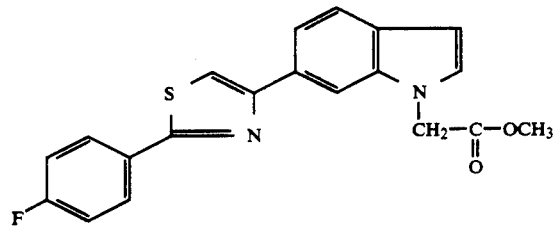

In an analogous manner to Example (IV-1), methyl [6-[2-(4-fluorophenyl)-thiazol-4-yl]-indol-1-yl]-acetate is obtained.

Example (IV-3)

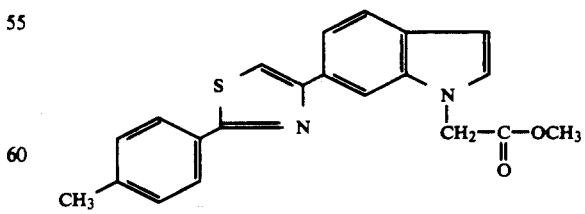

In an analogous manner to Examples (IV-1) and (IV-2), methyl [6-[6-(4-methylphenyl)-thiazol-4-yl]indol-1-yl]-acetate of melting point m.p.: 100°–102° C. is obtained.

The compounds of the formula (IV)

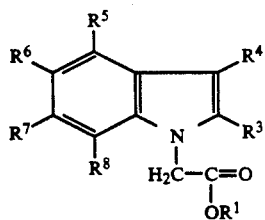

(IV)

shown in the following Table 3 can be prepared analogously to Examples (IV-1) to IV-3) and in accordance with the general information on the process.

Example (XI-1)

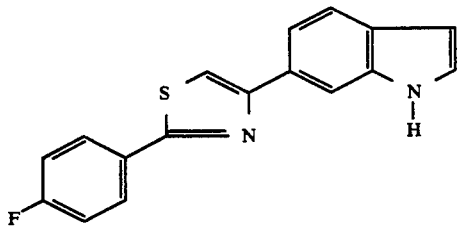

A solution of crude β-dimethylamino-4-[2-(4-fluorophenyl)-thiazol-4-yl]-2-nitrostyrene in 200 ml of tetrahydrofuran is treated with 5 g of Raney nickel, and the

TABLE 3

| Example No. | $R^1$ | $R^3$ | $R^4$ | $R^5$ | $R^6$ | $R^7$ | $R^8$ | physical data |
|---|---|---|---|---|---|---|---|---|
| (IV-4) | $CH_3$ | H | H | H | H | 2-ethyl-pyridyl-thiazolyl | H | m.p. 57–58° C. |
| (IV-5) | $CH_3$ | H | H | H | H | 2,3-dichlorophenyl-thiazolyl | H | $n_D^{20}$ 1.5955 |
| (IV-6) | $CH_3$ | H | H | H | H | 3,4-dichlorophenyl-thiazolyl | H | m.p. 108–109° C. |
| (IV-7) | $CH_3$ | H | H | H | H | pyridyl-thiazolyl | H | $n_D^{20}$ 1.5978 |
| (IV-8) | $CH_3$ | H | H | H | H | 3-chlorophenyl-thiazolyl | H | m.p. 121–122° C. |
| (IV-9) | $CH_3$ | H | H | H | H | 3-phenoxyphenyl-thiazolyl | H | m.p. 98–99° C. |
| (IV-10) | $CH_3$ | H | H | H | H | 4-methoxyphenyl-thiazolyl | H | m.p. 106–107° C. |
| (IV-11) | $CH_3$ | H | H | H | H | 4-methoxyphenyl-thiazolyl | H | m.p. 108–109° C. | mixture is hydrogenated for 4.5 hours at 70° C. at a hydrogen pressure of 50-60 bar. For working up, the mixture is filtered, the filtrate is concentrated, and the residue is chromatographed on silica gel (eluent dichloromethane).

10.33 g (43.5% of theory) of 6-[2-(4-fluorophenyl)-thiazol-4-yl]-indole of melting point m.p. 139°-140° C. are obtained.

Example (XI-2)

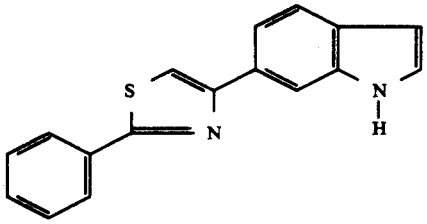

In an analogous manner to Example (XI-1), 6-(2-phenyl-thiazol-4-yl)-indole of melting point m.p.: 159°-161° C. is obtained.

Example (XI-3)

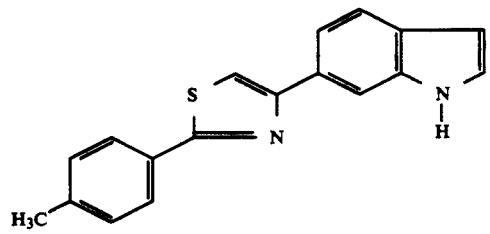

In an analogous manner to Examples (XI-1) and (XI-2), 6-[2-(4-methylphenyl)-thiazol-4-yl]-indole of melting point m.p. 177° C. is obtained.

The compounds of the formula (XI)

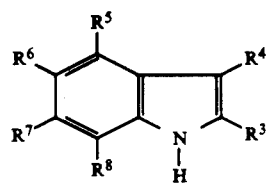

(XI)

shown in the following Table 4 can be prepared analogously to Examples (XI-1) to (XI-3) and in accordance with the general information on the process

TABLE 4

| Example No. | $R^3$ | $R^4$ | $R^5$ | $R^6$ | $R^7$ | $R^8$ | physical data |
|---|---|---|---|---|---|---|---|
| (XI-4) | H | H | H | H | 4-CH₃O-C₆H₄-C(=N-)-S- | H | m.p. 110-111° C. |
| (XI-5) | H | H | H | H | 2,3-Cl₂-C₆H₃-C(=N-)-S- | H | |
| (XI-6) | H | H | H | H | 3,4-Cl₂-C₆H₃-C(=N-)-S- | H | m.p. 98-99° C. |
| (XI-7) | H | H | H | H | 2-C₂H₅-pyridin-4-yl-C(=N-)-S- | H | m.p. 109-110° C. |
| (XI-8) | H | H | H | H | pyridin-2-yl-C(=N-)-S- | H | m.p. 156° C. |
| (XI-9) | H | H | H | H | 3-Cl-C₆H₄-C(=N-)-S- | H | m.p. 136° C. |

TABLE 4-continued

| Example No. | R³ | R⁴ | R⁵ | R⁶ | R⁷ | R⁸ | physical data |
|---|---|---|---|---|---|---|---|
| (XI-10) | H | H | H | H | 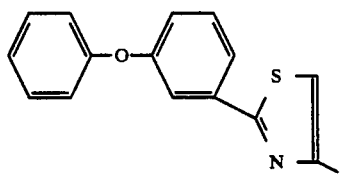 | H | m.p. 108–109° C. |
| (XI-11) | H | H | H | H | 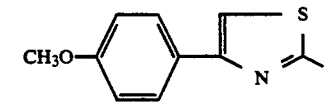 | H | m.p. 164–165° C. |
| (XI-12) | H | H | H | H | 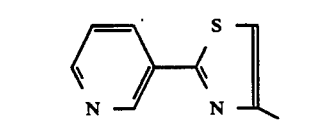 | H | MS: m/e 277 (M⁺) |

EXAMPLE (XV-1)

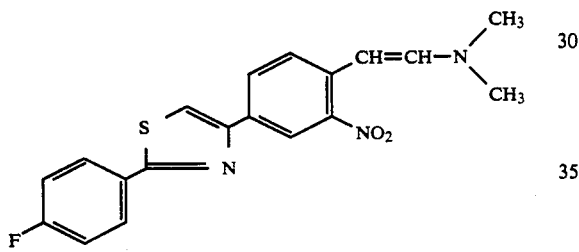

A mixture of 25.38 g (50.76 mmol) of 2-methyl-5-[2-(4-fluorophenyl)-thiazol-4-yl]-nitrobenzene, 84.00 g (704.87 mmol) of dimethylformamide dimethyl acetal and 120 ml of dimethylformamide is refluxed for approximately 18 hours until the reaction is complete. The end of the reaction is determined by means of thin-layer chromatography. When the reaction is complete, the volatile constituents are first removed under a water-pump vacuum and then under an oil-pump vacuum. The black-red oil which remains is employed in the next reaction step without further purification.

Upon prolonged standing, β-dimethylamino-4-[2-(4-fluorophenyl)-thiazol-4-yl]-2-nitrostyrene is obtained as a crystalline product of melting point m.p.: 137°–138° C.

Example (XV-2)

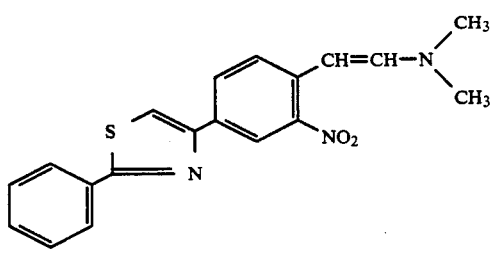

In an analogous manner to Example (XV-1), β-dimethylamino-4-(2-phenyl-thiazol-4-yl)-2-nitrostyrene is obtained

Example (XV-3)

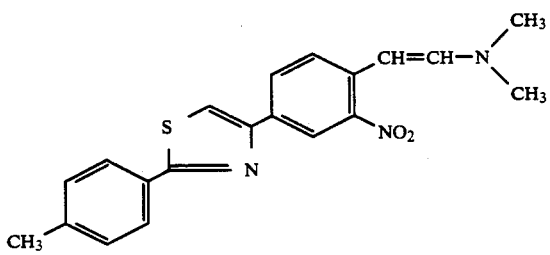

In an analogous manner to Example (XV-1) and Example (XV-2), β-dimethylamino-4-[-2-(4-methylphenyl)thiazol-4-yl]-2-nitrostyrene is obtained as a crystalline product of melting point m.p.: 124°–125° C.

The compounds of the formula (XV)

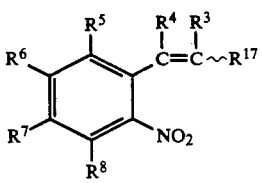

(XV)

shown in the following Table 5 can be prepared analogously to Examples (XV-1) to (XV-3) and in accordance with the information on the process.

TABLE 5
| Example No. | R³ | R⁴ | R⁵ | R⁶ | R⁷ | R⁸ | R¹⁷ | physical data |
|---|---|---|---|---|---|---|---|---|
| (XV-4) | H | H | H | H | 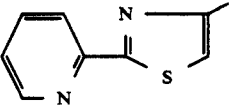 | H | N(CH₃)₂ | m.p. 130° C. |
| (XV-5) | H | H | H | H | 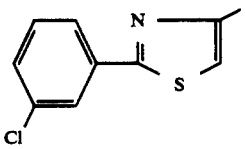 | H | N(CH₃)₂ | m.p. 114° C. |
| (XV-6) | H | H | H | H | 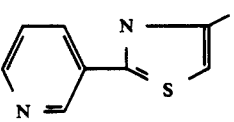 | H | N(CH₃)₂ | m.p. 147° C. |
| (XV-7) | H | H | H | H | 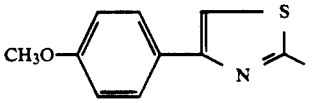 | H | N(CH₃)₂ | MS: m/e 381 (M⁺) |
| (XV-8) | H | H | H | H | 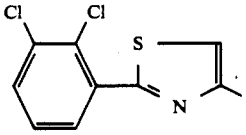 | H | N(CH₃)₂ | MS: m/e 419 (M⁺-H) |
| (XV-9) | H | H | H | H | 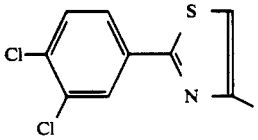 | H | N(CH₃)₂ | MS: m/e 419 (M⁺-H) |
| (XV-10) | H | H | H | H | 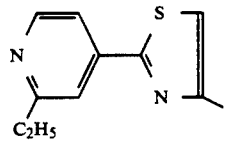 | H | N(CH₃)₂ | MS: m/e 380 (M⁺) |
| (XV-11) | H | H | H | H | 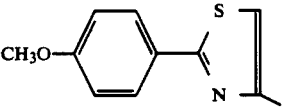 | H | N(CH₃)₂ | MS: m/e 381 (M⁺) |
| (XV-12) | H | H | H | H | 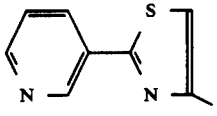 | H | N(CH₃)₂ |  |
| (XV-13) | H | H | H | H | 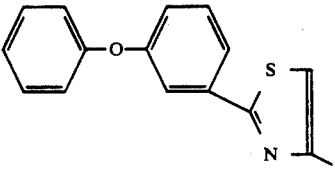 | H | N(CH₃)₂ | MS: m/e 443 (M⁺) |

Example (XIII-1)

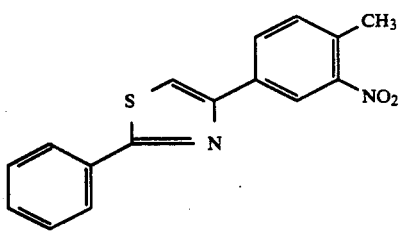

A mixture of 23.79 g (92.2 mmol) of 4-methyl-3-nitrophenacyl bromide, 18.61 g (135.6 mmol) of thiosbenzamide and 350 cm³ of ethanol is refluxed for approximately 1 hour, with stirring. The mixture is allowed to cool, and the crystals which precipitate out are filtered off with suction.

26.46 g (96.8% of theory) of 2-methyl-5-(2-phenyl-thiazol-4-yl)-nitrobenzene of melting point m.p.: 97°–98° C. are obtained.

Example (XII-2)

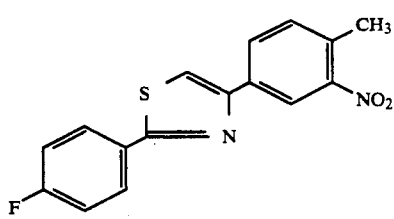

In an analogous manner to Example (XIII-1), 2-methyl-5-[2-(4-fluorophenyl)-thiazol-4-yl]-nitrobenzene of melting point m.p.: 124° C. is obtained.

Example (XIII-3)

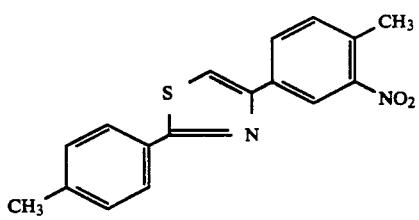

In an analogous manner to Examples (XIII-1) and (XIII-2), 2-methyl-5-[2-(4-methylphenyl)-thiazol-4-yl]-nitrobenzene of melting point m.p.: 104° C. is obtained.

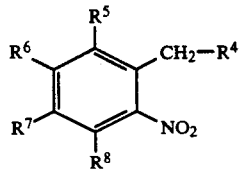

(XIII)

shown in the following Table 6 can be prepared analogously to Examples (XIII-1) to (XIII-3) and in accordance with the information in the process.

TABLE 6

| Example No. | $R^4$ | $R^5$ | $R^6$ | $R^7$ | $R^8$ | physical data |
|---|---|---|---|---|---|---|
| (XIII-4) | H | H | H | Cl, Cl, (2,3-dichlorophenyl-thiazolyl) | H | m.p. 164° C. |
| (XIII-5) | H | H | H | Cl, Cl (3,4-dichlorophenyl-thiazolyl) | H | m.p. 164° C. |
| (XIII-6) | H | H | H | $C_2H_5$ (ethylpyridyl-thiazolyl) | H | m.p. > 240° C. |
| (XIII-7) | H | H | H | Cl (3-chlorophenyl-thiazolyl) | H | m.p. > 240° C. |
| (XIII-8) | H | H | H | (pyridyl-thiazolyl) | H | m.p. > 240° C. |

TABLE 6-continued

| Example No. | R⁴ | R⁵ | R⁶ | R⁷ | R⁸ | physical data |
|---|---|---|---|---|---|---|
| (XIII-9) | H | H | H | [phenyl-O-phenyl-C(=N-)-S-] | H | m.p. 106–107° C. |
| (XIII-10) | H | H | H | [pyridyl-C(=N-)-S-] | H | m.p. 135° C. |
| (XIII-11) | H | H | H | [CH₃O-phenyl-C(=N-)-S-(CH₃)] | H | m.p. 108–109° C. |
| (XIII-12) | H | H | H | [CH₃O-phenyl-C(=N-)-S-] | H | MS: m/e 326 (M⁺) |
| (XIII-13) | H | H | H | [pyridyl-C(=N-)-S-] | H | ¹H-NMR:*δ=2.56(S, CH₃) 7.63–9.45 (m, 8H) |

*The ¹H-NMR-spectra were recorded in deuterochloroform (CDCl₃) with tetramethylsilan (TMS) as the internal standard. The chemical shift as the δ-value in ppm is stated.

USE EXAMPLES

In the following Use Examples, the compound given below was employed as comparison substance:

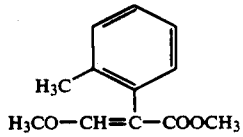

(A)

H₃CO—CH=C—COOCH₃ methyl 3-methoxy-2-(2-methylphenyl)-acrylate (disclosed in European Patent 178,816).

EXAMPLE A

Pyricularia Test (Rice)/Protective

Solvent: 12.5 parts by weight of acetone.
Emulsifier: 0.3 part by weight of alkylaryl polyglycol ether.

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds of Preparation Examples (1) (Z-isomer), (1) (Z/E-isomer mixture), (2) (Z-isomer), (2) (Z/E-isomer mixture), (IV-3), (IV-4), (IV-5), (IV-6) and (IV-10).

EXAMPLE B

Cochliobolus Sativus Test (Barley)/Protective

Solvent: 100 parts by weight of dimethylformamide.
Emulsifier: 0.25 part by weight of alkylaryl polyglycol ether.

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound until dew-moist. After the spray coating has dried, on, the plants are sprayed with a conidia suspension of Cochliobolus sativus. The plants remain in an incubation cabin at 20° C. and 100% relative atmospheric humidity for 48 hours.

The plants are placed in a greenhouse at a temperature of approximately 20° C. and a relative atmospheric humidity of approximately 80%.

Evaluation if carried out 7 days after the inoculation.

In this test, a clearly superior activity compared with the prior art is shown, for example, by the compounds (2) (Z-isomer) and (2) (Z/E-isomer mixture) according to the Preparation Examples.

EXAMPLE C

Pyrenophor Teres Test (Barley)/Protective

Solvent: 100 parts by weight of dimethylformamide.
Emulsifier: 0.25 part by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conida suspension of *Pyrenophora teres*. The plants remain in an incubation cabin at 20° C. and 100% relative atmospheric humidity for 48 hours.

The plants are placed in a greenhouse at a temperature of approximately 20° C. and a relative atmospheric humidity of approximately 80%.

Evaluation is carried out 7 days after the inoculation.

In this test, a clearly superior activity compared with the prior art is shown, for example, by the compounds of Preparation Examples (2) (Z-isomer), (2) (Z/E-isomer mixture), (IV-1) and (IV-3).

EXAMPLE D

Phytophthora Test (Tomato)/Protective

Solvent: 4.7 parts by weight of acetone.
Emulsifier: 0.3 part by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabin at 100% relative atmospheric humidity and approximately 20° C.

Evaluation is carried out 3 days after the inoculation.

In this test, a clearly superior activity compared with the prior art is shown, for example, by the compounds of Preparation Examples (1) (Z/E-isomer mixture), (2) (Z-isomer) and (2) (Z/E-isomer mixture).

EXAMPLE E

Venturia Test (Apple)/Protective

Solvent: 4.7 parts by weight of acetone.
Emulsifier: 0.3 part by weight of alkylaryl polyglycol ether.

To produce a suitable preparation of active compound, 1 part by weight of active compound is mixed with the stated amounts of solvent and emulsifiers and the concentrate is diluted with water to the desired concentration.

To test for protective activity, young plants are sprayed with the preparation of active compound until dripping wet. After the spray coating has dried on, the plants are inoculated with an aqueous conidia suspension of the pathogen causing apple scab (*Venturia inaequalis*) and then remain in an incubation cabin at 20° C. and 100% relative atmospheric humidity for 1 day.

The plants are then placed in a greenhouse at 20° C. and a relative atmospheric humidity of approximately 70%.

Evaluation is carried out 12 days after the inoculation.

In this test, a clearly superior activity compared with the prior art is shown, for example, by the compounds of Preparation Examples (1) (Z-isomer), (1) (Z/E-isomer mixture), (2) (Z-isomer) and (2) (Z/E-isomer mixture).

EXAMPLE F

Spodoptera Test

Solvent: 3 parts by weight of dimethylformamide.
Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water containing emulsifier to the desired concentrations.

Soy bean plants (*Glycine soja*) are treated with the active compound preparation of the desired concentration. In a ten-fold replication, a single leaf of the treated plant is placed in a plastic tin and infested with in each case one larva ($L_2$) of the army worm (*Spodoptera frugiperda*). After 3 days, a further leaf of the corresponding plant is fed, depending on the dose. On day 7, the larvae are transferred to untreated artificial feed.

After the specified period of time, the destruction in % is determined. 100% means that all animals were destroyed; 0% means that no animals have been destroyed.

In this test, a superior activity compared with the prior art is shown, for example, by the following compounds of the Preparation Examples: (1) (Z-isomer), (1) (Z/E-isomer mixture), (2) (Z-isomer) and (3).

EXAMPLE G

Plutella Test

Solvent: 3 parts by weight of dimethylformamide.
Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water containing emulsifier to the desired concentrations.

Cabbage plants (*Brassica oleracea*) are treated with the active compound preparation of the desired concentration. A leaf of the treated plant is placed in a plastic tin and infested with larvae ($L$,) of the cabbage moth (*Plutella xylostella*). After 2 and 4 days, a further leaf of the same plant is used in each case for subsequent feeding.

After the specified period of time, the destruction in % is determined. 100% means that all animals have been destroyed; 0% means that no animals have been destroyed.

In this test, for example the following compounds of the Preparation Examples show a superior activity compared with the prior art: (1) (Z-isomer), (1) (Z/E-isomer mixture), (2) (Z-isomer), (2) (Z/E-isomer mixture) and (3).

EXAMPLE H

Phaedon Test

Solvent: 3 parts by weight of dimethylformamide.

Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water containing emulsifier to the desired concentrations.

Cabbage plants (*Brassica oleracea*) are treated with the active compound preparation of the desired concentration. A leaf of the treated plant is placed in a plastic tin and infested with larvae (L,) of the mustard beetle (*Phaedon cochleariae*). After 2 and 4 days, a further leaf of the same plant is used in each case for subsequent feeding.

After the specified period of time, the destruction in % is determined. 100% means that all animals have been destroyed; 0% means that no animals have been destroyed.

In this test, for example the following compounds of the Preparation Examples show a superior activity compared with the prior art:(1) (Z-isomer), (1) (Z/E-isomer mixture), (2) (Z-isomer), (2) (Z/E-isomer mixture) and (3).

EXAMPLE I

Myzus Test

Solvent: 3 parts by weight of dimethylformamide.

Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water containing emulsifier to the desired concentrations.

Cabbage plants (*Brassica oleracea*) which are infested with the green peach aphid (*Myzus persicae*) are sprayed with the desired concentration of the active compound preparation until dripping wet.

After the specified period of time, the action in is determined. 100% means that all animals have been destroyed; 0% means that no animals have been destroyed.

In this test, for example the following compounds of the Preparation Examples show a superior activity compared with the prior art:(1) (Z/E-isomer mixture), (2) (Z-isomer) and (3).

It will be appreciated that the instant specification s set forth by way of illustration and not limitation, and that various modifications and changes may be made without departing from the spirit and scope of the present invention.

What is claimed is:

1. A ketocarboxylic acid derivative of the formula

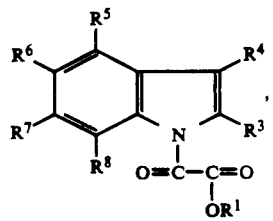

(VI)

in which
$R^1$ represents straight-chain or branched alkyl having 1 to 6 carbon atoms, or represents benzyl, $R^3$ and $R^4$ in each case independently of one another represent hydrogen, cyano, fluorine, chlorine, bromine or straight-chain or branched alkyl having 1 to 6 carbon atoms, $R^5$, $R^6$ and $R^8$ independently of one another represent hydrogen, fluorine, chlorine, bromine, methyl, ethyl, n- or i-propyl, n-, i-, s- or t-butyl, methoxy, ethoxy, n- or i-propoxy, methylenedioxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoxyiminoethyl, cyclopentyl, cyclohexyl, divalent 1,3-propanediyl or 1,4-butanediyl, or represnts phenyl, benzyl, phenoxy, benzyloxy, phenylthio or benzylthio, each of which is optionally monosubstituted or trisubstituted in the phenyl moiety by identical or different substituents from the group consisting of fluorine, chlorine, bromine, methyl, ethyl, methoxy, ethoxy, methylthio, trifluoromethyl, difluoromethoxy, trifluoromethoxy and trifluoromethylthio, and $R^7$ represents

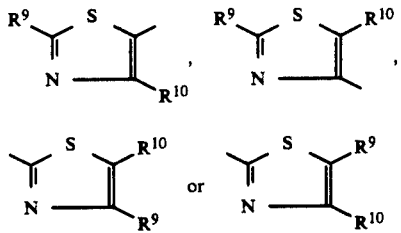

where
$R^9$ and $R^{10}$ in each case independently of one another represent hydrogen, fluorine, chlorine, bromine, cyano, in each case straight-chain or branched alkyl, alkoxy, alkylthio or halogenoalkyl having 1 to 6 carbon atoms and where appropriate 1 to 13 identical or different halogen atoms, or represent straight-chain or branched alkoxycarbonyl having 1 to 6 carbon atoms in the alkoxy moiety, or dialkylaminocarbonyl which has 1 to 4 carbon atoms in each alkyl moiety, each of the individual alkyl moieties being straight-chair on branched and substituted by identical or different substituents, or represents phenyl, benzyl, phenyloxy, phenylthio, benzyloxy or benzylthio, each of which is unsubstituted or monosubstituted to trisubstituted by identical or different substituents, or represent 5- or 6-membered heteroaryl which contains 1 to 3 hetero atoms from the group consisting of nitrogen, oxygen and sulphur and which is unsubstituted or monosubstituted or distributed by identical or different substituents, the substituents in each case being halogen, alkyl, alkoxy, alkylthio, halogenoalkyl, halogenoalkyloxy, halogenoalylthio, each of which has 1 to 4 carbon atoms and where appropriate 1 to 9 identical or different halogen atoms, dialkylamino or dialkylaminocarbonyl, each of which has 1 to 4 carbon atoms in each of the straight-chain or branched alkyl moieties, 1,3-propanediyl, 1,4-butanediyl, or phenyl or benzyl which are unsubstituted or monosubstituted to disubstituted by identical or different substituents selected from the group consisting of halogen and phenyloxy.

2. A ketocarboxylic acid derivative according to claim 1, in which $R^1$ represents straight-chain or branched alkyl having 1 to 4 carbon atoms,

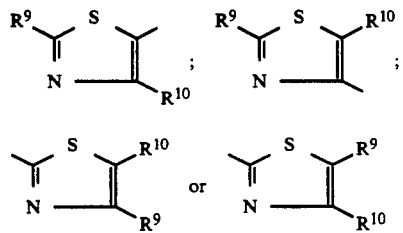

where $R^9$ represents hydrogen, straight-chain or branched alkyl having 1 to 6 carbon atoms, or phenyl or benzyl, each of which is optionally monosubstituted to trisubstituted by identical or different substituents, or represents 5- or 6-membered heteroaryl which contains 1 to 3 hetero atoms from the group consisting of nitrogen, oxygen and sulphur, and which is optionally monosubstituted or disubstituted by identical or different substituents, the optional substituents in each case being selected from the group consisting of halogen, methyl, ethyl, n- or i-propyl, n-i-, s- or t-butyl, methoxy, ethoxy, n- or i-propoxy, n-, i-, s- or t-butoxy, methylthio, ethylthio, n- or i-propylthio, n-, i-, s- or t-butylthio, halogenoalkyl, halogenoalkoxy or halogenoalkylthio, each of which has 1 or 2 carbon atoms and 1 to 5 identical or different fluorine or chlorine atoms, dialkylamino or dialkylaminocarbonyl having 1 or 2 carbon atoms in the individual alkyl moieties, and phenyl, phenoxy or benzyl which are unsubstituted or monosubstituted to disubstituted by identical or different substituents selected from the group consisting of fluorine, chlorine or phenoxy, and $R^{10}$ represents hydrogen, straight-chain or branched alkyl having 1 to 4 carbon atoms, chlorine, bromine, cyano, methoxycarbonyl, ethoxycarbonyl, dimethylaminocarbonyl, diethylaminocarbonyl, methoxy, ethoxy, methylthio or ethylthio, and $R^8$ represents hydrogen, fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl or ethoxycarbonyl.

3. A ketocarboxylic acid derivative according to claim 1, in which $R^1$ represents methyl or ethyl, $R^3$ represents hydrogen, chlorine or methyl, $R^4$ represents hydrogen, chlorine or methyl, $R^5$ represents hydrogen, fluorine, chlorine, bromine, methyl, ethyl, trifluoromethyl, methoxycarbonyl or ethoxycarbonyl, $R^6$ represents hydrogen, fluorine, chlorine, bromine, methyl, ethyl, methoxy, ethoxy, methylthio, trifluoromethyl, methoxycarbonyl or ethoxycarbonyl, or $R^5$ and $R^6$ together represent a methylenedioxy, 1,3-propanediyl or 1,4-butanediyl group, $R^7$ represents

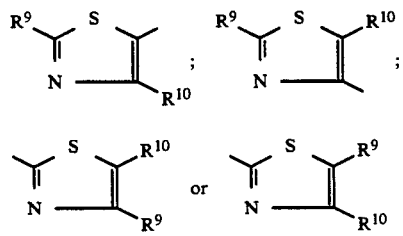

where $R^9$ represents hydrogen, methyl, ethyl, n- or i-propyl, n-, s-, i-butyl, n- or i-pentyl, n-hexyl, benzyl, o-, m- or p-chlorobenzyl, o-, m- or p-methylbenzyl, phenyl or phenyl which is monosubstituted to trisubstituted by identical or different substituents, or represent 5- or 6-membered heteroaryl which contains 1 or 2 hetero atoms from the group consisting of nitrogen, oxygen and sulphur and which is monosusbituted or disubstituted by identical or different substituents, the the phenyl or heteroaryl substituents in each case being fluorine, chlorine, methyl, ethyl, t-butyl, methoxy, ethoxy, methylthio, trifluoromethyl, trifluoromethoxy, trifluoromethylthio, phenyl, p-chlorophenyl, m- or p-phenoxyphenyl or benzyl, and $R^{10}$ represents hydrogen, methyl, ethyl, chlorine, bromine, methoxycarbonyl or ethoxycarbonyl, and $R^8$ represents hydrogen, methyl or ethyl.

* * * * *

UNITED STATES PATENT AND TRADEMARK OFFICE
CERTIFICATE OF CORRECTION

PATENT NO. : 5,292,889
DATED : March 8, 1994
INVENTOR(S) : Alexander Klauseneer, et al.

It is certified that error appears in the above-indentified patent and that said Letters Patent is hereby corrected as shown below:

Column 65, line 19, after "atoms" insert --$R^3$ and $R^4$ are identical or different and represent hydrogen, cyano, fluorine, chlorine, bromine, methyl, ethyl, n- or i-propyl or n-, i-, s- or t-butyl, $R^5$ and $R^6$ are identical or different and represent hydrogen, fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoxyiminomethyl, methoximinoethyl, ethoxyiminoethyl, cyclopentyl or cyclohexyl, or together represent a methylenedioxy, 1,3-propanediyl or 1,4-butanediyl group, $R^7$ represents--

Signed and Sealed this

Twenty-sixth Day of October, 1999

*Attest:*

Q. TODD DICKINSON

*Attesting Officer*     *Acting Commissioner of Patents and Trademarks*